US011666635B2

United States Patent
Sjögren et al.

(10) Patent No.: US 11,666,635 B2
(45) Date of Patent: *Jun. 6, 2023

(54) STABLE LIQUID GONADOTROPIN FORMULATION

(71) Applicant: Ferring B.V., Hoofddorp (NL)

(72) Inventors: Helen Ulrika Sjögren, Lund (SE); Charlotte Hojer-Pedersen, Viby Sjaelland (DK)

(73) Assignee: Ferring B.V., Hoofddorp (NL)

( * ) Notice: Subject to any disclaimer, the term of this patent is extended or adjusted under 35 U.S.C. 154(b) by 185 days.

This patent is subject to a terminal disclaimer.

(21) Appl. No.: 17/020,279

(22) Filed: Sep. 14, 2020

(65) Prior Publication Data

US 2021/0236600 A1    Aug. 5, 2021

Related U.S. Application Data

(63) Continuation of application No. 16/079,428, filed as application No. PCT/EP2017/054325 on Feb. 24, 2017, now Pat. No. 10,792,334.

(30) Foreign Application Priority Data

Feb. 24, 2016 (GB) .................... 1603280

(51) Int. Cl.
  *A61K 38/24*    (2006.01)
  *A61K 9/00*     (2006.01)
  *A61K 47/18*    (2017.01)
  *A61K 9/08*     (2006.01)
  *A61P 15/08*    (2006.01)
  *A61K 47/10*    (2017.01)
  *A61K 47/26*    (2006.01)

(52) U.S. Cl.
  CPC ............ *A61K 38/24* (2013.01); *A61K 9/0019* (2013.01); *A61K 9/08* (2013.01); *A61K 47/10* (2013.01); *A61K 47/183* (2013.01); *A61K 47/26* (2013.01); *A61P 15/08* (2018.01)

(58) Field of Classification Search
  None
  See application file for complete search history.

(56) References Cited

U.S. PATENT DOCUMENTS

| 5,929,028 | A  | 7/1999  | Skrabanja et al. |
| 10,792,334 | B2 | 10/2020 | Sjögren et al. |
| 2015/0071879 | A1 | 3/2015 | Jezek et al. |
| 2016/0319011 | A1 | 11/2016 | Gokarn et al. |

FOREIGN PATENT DOCUMENTS

| CN | 1165341 A | 11/1997 | |
| CN | 1309567 A | 8/2001 | |
| CN | 101842083 A | 9/2010 | |
| CN | 102821782 A | 12/2012 | |
| CN | 103052398 A | 4/2013 | |
| CN | 110433136 A | 11/2019 | |
| EP | 0 974 359 A2 | 1/2000 | |
| EP | 2 219 607 A1 | 8/2010 | |
| EP | 2 417 982 A1 | 2/2012 | |
| EP | 2 533 800 B1 | 12/2012 | |
| JP | 2002-521342 A | 7/1999 | |
| JP | 2009-509953 A | 3/2009 | |
| JP | 2011-502968 A | 1/2011 | |
| JP | 2013-532677 A | 8/2013 | |
| JP | 2016-534061 A | 11/2016 | |
| RU | 2659431 C2 | 2/2018 | |
| WO | WO 2006/138181 | * 12/2006 | ........... A61K 39/395 |
| WO | WO 2009/056569 A1 | 5/2009 | |
| WO | WO 2011/099036 A2 | 8/2011 | |
| WO | WO 2011/108010 A2 | 9/2011 | |
| WO | WO 2015/075743 A1 | 5/2015 | |

OTHER PUBLICATIONS

Gleicher and Karande, Journal of Assisted Reproduction and Genetics, 2000: vol. 17, No. 9 (Year: 2000).*
Chang et al., Boehringer Ingelheim, Fremont, CA, USA, 253rd ACS National Meeting & Exposition, San Francisco, CA, United States, Apr. 2-6, 2017 (2017), BIOT-262. American Chemical Society: Washington, D.C. (Year: 2017).*
International Search Report and Written Opinion dated Jul. 26, 2017 in connection with PCT/EP2017/054325.
Dahl et al., The effect of buffering of acetylsalicylic acid on dissolution, absorption, gastric pH and faecal blood loss. International Journal of Pharmaceutics. Feb. 1982;10(2):143-51.
No Author Listed] Synonyms for "surfactant" from English Thesaurus [online] Retrieved Feb. 26. https://englishthesaurus.net/synonym/surfactant, 2020.
Phero et al., A Comparison of Buffered and Non-Buffered 2% Lidocaine With Epinephrine, a Pilot Study. J Oral Maxillofac Surg. Sep. 2016;74(9):e41.
Reddy et al. L-Arginine increases the solubility of unfolded species of hen egg white lysozyme. Protein Sci. Apr. 2005;14(4):929-35. doi: 10.1110/ps.041085005. Epub Mar. 1, 2005.
PCT/EP2017/054325, Jul. 26, 2017, International Search Report and Written Opinion.

* cited by examiner

*Primary Examiner* — Christina M Borgeest
(74) *Attorney, Agent, or Firm* — Wolf, Greenfield & Sacks, P.C.

(57) ABSTRACT

The present invention pertains in general to the field of the stabilization of gonadotropin formulations, in particular liquid formulations of gonadotropins. The stabilization is achieved by a particular combination of excipients, preferably arginine and methionine. In a preferred embodiment, the formulation does not comprise a buffer.

22 Claims, 2 Drawing Sheets

Figure 1:
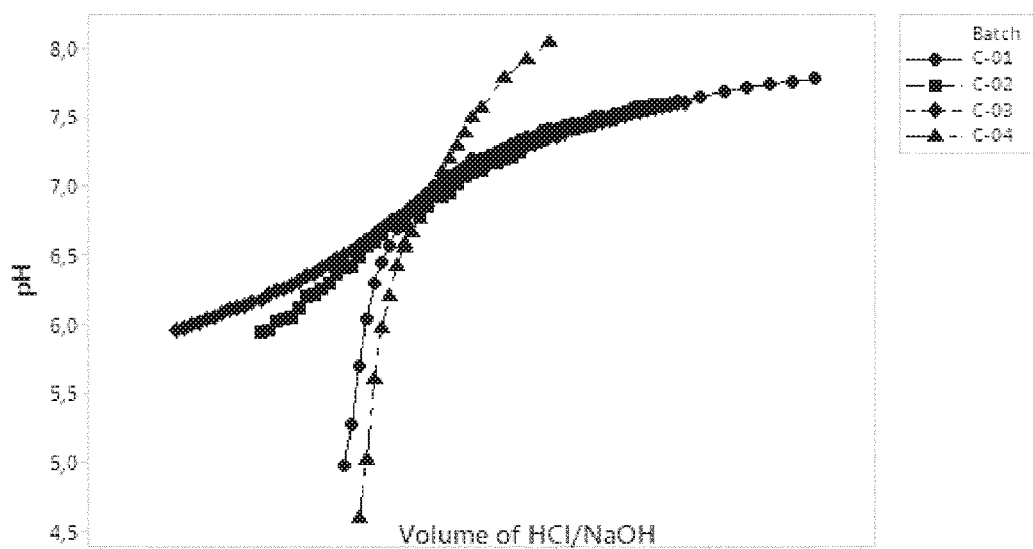

Specification includes a Sequence Listing.

STABLE LIQUID GONADOTROPIN FORMULATION

RELATED APPLICATIONS

This application is a Continuation application of U.S. application Ser. No. 16/079,428, filed Aug. 23, 2018 (Allowed), which is a National stage filing under 35 U.S.C. § 371 of International Application Number PCT/EP2017/054325, filed Feb. 24, 2017, and claims priority to Great Britain Application Number 1603280.7, filed Feb. 24, 2016, each of which is herein incorporated by reference in its entirety.

FIELD OF THE INVENTION

The present invention pertains in general to the field of the stabilization of gonadotropin formulations, in particular liquid formulations of gonadotropins. The stabilization is achieved by a particular combination of excipients, preferably arginine and methionine. In a preferred embodiment, the formulation does not comprise a buffer.

BACKGROUND

Gonadotropins are a family of hormones, which are essentially and mainly involved in the fertility cycle in females and males. Gonadotropins can be derived from urine, both for research and treatment purposes, however, several gonadotropins like e.g., hCG, LH and FSH, can also be produced recombinantly.

In particular, gonadotropins can be employed in the treatment of infertility.

The four main gonadotropins all belong to the same glycoprotein family. These are follicle stimulating hormone (FSH), thyroid stimulating hormone (TSH), luteinizing hormone (LH) and (human) chorionic gonadotropin (hCG). All of these gonadotropins are heterodimeric and consist of an alpha and a beta subunit; the alpha subunit is common to all, i.e. the same for all above-mentioned four gonadotropins, while the beta subunit differs, respectively. The action of FSH is mediated by a distinct FSH receptor. The beta chains of LH and HCG share 82% protein sequence homology and exert their actions through the same LH receptor.

FSH is naturally secreted by the anterior pituitary gland and functions to support follicular development and ovulation. FSH comprises a 92 amino acid alpha subunit, also common to the other glycoprotein hormones, e.g. LH and hCG, and a 111 amino acid beta subunit unique to FSH that confers the biological specificity of the hormone (Pierce and Parsons, 1981, Glycoprotein hormones: structure and function, Ann Rev Biochem., 50: 465-495). The mature beta subunit of hCG is composed of 145 amino acids. Each subunit in FSH and hCG is post-translationally modified by the addition of complex carbohydrate residues. For FSH, both subunits carry two sites for N-linked glycan attachment, the alpha subunit at amino acids 52 and 78 and the beta subunit at amino acid residues 7 and 24 (Rathnam and Saxena, (1975) *Primary amino acid sequence of follicle stimulating hormone from human pituitary glands. I. alpha subunit*, J Biol Chem. 250 (17):6735-6746; Saxena and Rathnam, (1976) *Amino acid sequence of the beta subunit of follicle-stimulating hormone from human pituitary glands*, J Biol Chem. 251(4): 993-1005)). FSH is thus glycosylated to about 30% by mass (Dias and Van Roey, (2001) Structural biology of human follitropin and its receptor. Arch Med Res. 32(6): 510-519; Fox et al. (2001) Three-dimensional structure of human follicle-stimulating hormone. Mol Endocrinol. 15(3), 379-89). The beta subunit of hCG contains both N- and O -glycosylation (N-13, N-30, O-121, O-127, O-132 and O-138). The extra glycosylation in the beta subunit of hCG makes it more hydrophilic than that of FSH. ß-subunits provide specificity for the receptor interaction.

Urinary derived gonadotropins have been used clinically for over 40 years and their safety is well established. New generations of highly purified (HP) urinary derived gonadotropin compared with the first generation have been introduced over time. The increased purity is obtained by adding additional purification steps, such as anion exchange and hydrophobic interaction chromatography steps to remove urinary proteins without FSH and/or LH bioactivity. The significantly increased purity of the new generation gonadotropin preparations facilitates more comprehensive characterization studies providing additional information on the composition.

Purified urinary FSH and human menopausal menotropins (hMG), both isolated from the urine of post-menopausal women, have been used for many years in infertility treatment either to induce (mono) ovulation or to stimulate multiple follicles in patients undergoing controlled ovarian stimulation (COS) prior to assisted reproduction technologies (ART). Two recombinant versions of FSH, Gonal-F® (follitropin alpha, Merck Serono) and Puregon®/Follistim® (follitropin beta, Merck) became available in the mid-1990s. Both products are expressed in Chinese hamster ovary (CHO) cell lines (Howles, C. M. (1996), *genetic engineering of human FSH (Gonal-f)*, Hum Reprod. Update, 2: 172-191).

CHO cells are commonly used for the production of pharmaceutical recombinant proteins. Structural analysis has identified that sialic acid is exclusively attached by an α2,3-linkage. Many human glycoproteins contain a mixture of both α2,3- and α2,6-linkages for sialic acid residues. Therefore, recombinant proteins expressed using the CHO system will differ from their natural counterparts in their type of terminal sialic acid linkages.

Infertility

In the present context, "infertility" shall be defined as the diminished ability or the inability to conceive and have offspring. Women who are able to get pregnant but then have repeat miscarriages are also said to be infertile. Infertility is also defined in specific terms as the failure to conceive after a year of regular intercourse without contraception. Infertility can be due to many causes. Studies have shown that a little more than half of cases of infertility are a result of female conditions. The remaining cases are caused by sperm disorders and by unexplained factors. There are currently several possibilities to treat infertility.

Those possibilities are a timed intercourse, the use of assisted reproductive technologies (ARTs), a medical management of endometriosis, ovulation induction (OI), fibroids and female sexual dysfunction (FSD), and surgery to correct abnormalities.

In assisted reproductive technology and OI, drugs to stimulate ovulation are used. Next to FSH, that is primarily responsible for the ovarian stimulation, gonadotropin preparations may contain LH and/or hCG.

Several different drug products containing gonadotropin hormones derived from urine of pregnant or postmenopausal women are currently used in clinical practice for the treatment of infertility, such as HMG (human menopausal gonadotropin) preparations containing a 1:1 ratio of FSH and LH bioactivity (see e.g. USP version 35, monograph for menotropins), as well as preparations containing only FSH bioactivity. From 1995 onwards, gonadotropin products, manufactured by recombinant DNA technology, have become available.

It is therefore important to provide stabilized formulations of such gonadotropin compounds, either alone or in a mixture.

Thus, it is an aim of the present invention to provide formulations, in particular liquid formulations, of one or more gonadotropins, particularly of a composition comprising hCG, optionally in a combination with FSH, which are stable. It is a further object of the present invention to provide a method for stabilization of such formulations. It is another object to provide such a formulation which is stable for 12 months, preferably for 24 months, even more preferably for 24 months at storage conditions plus 1 month "in use", i.e. at room temperature.

SUMMARY OF THE INVENTION

The present invention pertains to stable liquid gonadotropin formulations. In a preferred embodiment these formulations comprises hCG. In an also preferred embodiment, this formulation comprises both FSH and hCG. The gonadotropins in the formulations of the invention are preferably urinary-derived or plasma-derived, but can in an alternative embodiment be recombinantly produced.

In the following, the term "hMG" shall be used interchangeably with "gonadotropins from urine". Mostly, the gonadotropins from urine will be from human urine.

Human chorionic gonadotropin (hCG) contributes LH (luteinizing hormone) activity, which is responsible for presently approved pharmaceutical indications. This is a well known fact, and is described as part of the SmPCs of hMG preparations like the Menopur®-product, authorized for the same indications as presently claimed. Menopur®—in these SmPCs—comprises FSH and LH activity, but additionally confirms that hCG is responsible for at least part of the LH activity. Thus, any reference to hCG in the context of the present invention encompasses formulations which comprise an LH activity which is attributable to hCG.

Preferred embodiments include the following:

1. A liquid pharmaceutical gonadotropin formulation, comprising a gonadotropin, arginine in an amount of from 50 to 160 mM, and methionine in an amount of from 0.05 to 1.5 mg/ml, wherein the formulation does not comprise an additional buffer, and wherein the pH of the formulation is between 6.0 and 7.5.
2. The pharmaceutical formulation of item 1, wherein the gonadotropin comprises hCG (human chorionic gonadotropin), and optionally FSH and/or LH.
3. The pharmaceutical formulation of item 1 or 2, wherein the gonadotropin comprises hMG (human menopausal gonadotropin).
4. The pharmaceutical formulation of any one of items 1 to 3, wherein the gonadotropin (such as FSH, LH and/or hCG) is of human origin and urinary-derived.
5. The pharmaceutical formulation of any one of items 1 to 3, wherein the gonadotropin (such as FSH, LH and/or hCG) is recombinant.
6. The pharmaceutical formulation of any one of the preceding items, additionally comprising a preservative, preferably phenol.
7. The pharmaceutical formulation of any one of the preceding items, additionally comprising a surface-active agent, preferably a polysorbate, even more preferably polysorbate 20.
8. The pharmaceutical formulation of item 6 or 7, wherein the preservative, preferably the phenol, is present in an amount of 4-6 mg/ml, preferably in an amount of 5 mg/ml.
9. The pharmaceutical formulation of item 7 or 8, wherein the surface-active agent, preferably the polysorbate 20, is present in an amount of 0.001-0.05 mg/ml, preferably in an amount of 0.005 mg/ml.
10. The pharmaceutical formulation of any one of the preceding items, wherein the arginine is preferably L-arginine HCl.
11. The pharmaceutical formulation of any one of the preceding items, wherein the hMG is present in an amount of 300-900, more preferred 500-700, even more preferred 600-650, very preferably 625 IU/ml.
12. The pharmaceutical formulation of any one of the preceding items, which consists of
    625 IU/ml hMG
    0.15 mg/ml Methionine
    150 mM arginine
    5 mg/ml phenol
    0.005 mg/ml polysorbate 20
    Water for injection (WFI), and
    wherein the formulation has a pH of 6.8+/−0.3.
13. A liquid pharmaceutical formulation as described in any one of the preceding items, for use in a method of treatment of infertility.
14. The pharmaceutical formulation for the use of item 13, wherein the treatment is a treatment of ovulation induction (OI), assisted reproductive techniques (ART), and/or hypogonadotrophic hypogonadism in men.
15. A method for stabilization of a liquid pharmaceutical formulation, comprising hMG, which comprises the step of
    Providing a sample of urine from a human woman
    Extracting hMG
    Compounding said extract with arginine and methionine, in amounts as defined in any of the preceding items,
    Optionally further adding phenol and polysorbate in amounts as defined in any of the preceding items,
    Adjusting the pH to provide a formulation with a pH between 6.0 and 7.5,
    wherein no additional buffer is added.

As described above, gonadotropins, e.g. FSH and hCG as well as LH are suitable for the treatment of infertility. In that regard, it has become clear that liquid formulations of these gonadotropins can be unstable; this is true even for those gonadotropins which are destined for single use. Instability can be even more pronounced if the liquid formulations comprise a preservative, which is e.g. prescribed for all multidose formulations.

The present formulations may be destined for single-use or for multi-use, respectively.

The FSH formulated in the present formulations may be is urinary or plasma-derived or recombinant FSH (rFSH). In a preferred embodiment, the FSH is urinary or rFSH; particularly preferred it is urinary FSH.

As mentioned above, it is now possible to produce gonadotropins, like FSH, LH or hCG recombinantly. Thus, reference here to a gonadotropin in general always includes both the urinary- or plasma-derived as well as the recombinant (r) gonadotropin, unless otherwise specified. Thus, e.g. reference to "FSH" also encompasses rFSH. The production and amino acid sequences as well as the nucleic acid sequences of FSH, hCG and LH are all well-known to the person skilled in the art.

The sequences which can be used in the context of the present invention are as follows:
FSH, LH and hCG Alpha Subunit (SEQ ID NO:1)
(see also Fiddes, J. C. and Goodman, H. M. *The gene encoding the common alpha subunit of the four human glycoprotein hormones J. Mol. Appl. Genet.* 1 (1), 3-18 (1981))

```
MDYYRKYAAIFLVTLSVFLHVLHSAPDVQDCPECTLQENPFFSQPGAP
ILQCMGCCFSRAYPTPLRSKKTMLVQKNVTSESTCCVAKSYNRVTVMG
GFKVENHTACHCSTCYYHKS (116)
(underlined part is the leader peptide)
```

FSH Beta Subunit (SEQ ID NO:2)
(see also Saxena, B. B. and Rathnam, P. *Amino acid sequence of the beta subunit of follicle-stimulating hormone from human pituitary glands J. Biol. Chem.* 251 (4), 993-1005 (1976))

```
MKTLQFFFLFCCWKAICCNSCELTNITIAIEKEECRFCISINTTWCAG
YCYTRDLVYKDPARPKIQKTCTFKELVYETVRVPGCAHHADSLYTYPV
ATQCHCGKCDSDSTDCTVRGLGPSYCSFGEMKE (129)
(underlined part is the leader peptide)
``` hCG Beta Subunit (SEQ ID NO:3)
(see also Fiddes, J C, Goodman H M. *The cDNA for the beta-subunit of human chorionic gonadotropin suggests evolution of a gene by readthrough into the 3'-untranslated region Nature.* 1980 Aug. 14; 286(5774):684-7)

```
MEMFQGLLLLLLLLSMGGTWASKEPLRPRCR PINATLAVEK EGCPVCITVN TTICAGYCPT MTRVLQGVLP
ALPQVVCNYR DVRFESIRLP GCPRGVNPVV SYAVALSCQC ALCRRSTTDC GGPKDHPLTC DDPRFQDSSS
SKAPPPSLPS PSRLPGPSDT PILPQ (165)
(underlined part is the leader peptide)
```

LH Beta Subunit (SEQ ID NO:4)
(see also Sairam, M. R. and Li, C. H. *Human pituitary lutropin. Isolation, properties, and the complete amino acid sequence of the beta-subunit Biochim. Biophys. Acta* 412 (1), 70-81 (1975))

```
MEMLQGLLLLLLLSMGGAWASREPLRPWCH PINAILAVEKEGCPVCITVN
TTICAGYCPTMMRVLQAVLPPLPQVVCTYRDVRFESIRLPGCPRGVDPVVSFPVALSCRCGPCRRSTSDC
GGPKDHPLTC DHPQLSGLLFL (141)
(underlined part is the leader peptide)
```

In an alternative embodiment, the rFSH or the rHCG of all embodiments is a long-acting rFSH or rhCG, respectively. Such e.g. long-acting FSH formulations can be obtained as generally known to a person skilled in the art, e.g. by modifying the FSH molecule or by modifying the formulation.

"FSH" as used herein thus encompasses all possible urinary derived or recombinant forms of the above-mentioned FSH as well as all possible combinations of FSH forms. Also encompassed is a formulation for single use and one or more further formulations (of the same or a different gonadotropin) for multi-dose use.

One possible product may be a formulation including FSH (in a preferred embodiment also including hCG, and/or optionally LH, LH activity etc.), all in different containers. The LH activity, if present, may originate from LH or hCG. LH can be replaced by an equivalent dose of hCG and vice versa; an "equivalent dose" in that context can be calculated as is well known in the art.

A particularly preferred gonadotropin combination is that of FSH and hCG, preferably as an hMG formulation in one container, but optionally also e.g. in different containers, like e.g. vials or cartridges.

Possible combinations, which can be provided also in different containers, also include: urinary (u)FSH and uhCG or uFSH and uLH; further (rhCG or rLH or rFSH) and (uhCG or uLH or rhCG or rLH), and all possible permutations thereof. In a very preferred embodiment, the inventive formulation comprises FSH and hCG. In another equally preferred embodiment, the inventive formulation comprises hCG.

The gonadotropin formulations of the present invention are liquid formulations. Preferably, the formulation is injectable. Formulations can be supplied as a product having one, two or more pharmaceutical composition(s) including FSH or FSH/hCG, and/or LH, for administration separately or together. If administered separately, administration can be sequential. The product can be supplied in any appropriate package. For example, a product can contain a number of pre-filled syringes each including FSH (an FSH composition), or additionally hCG (an hCG composition) e.g. wherein the syringes can be packaged in a blister package or other means to maintain sterility. A product can optionally contain instructions for using the gonadotropin formulations.

According to a further aspect, the inventive gonadotropin formulation is provided as a multi-dose preparation. The present invention, however, explicitly is also directed to formulations destined for a single use. The present invention also pertains to a stabilization of formulations as part of a kit. Such a kit will comprise at least one container comprising one or more daily doses of the gonadotropin, e.g. FSH, or e.g. two containers (e.g. a vial), each comprising a different gonadotropin like hCG, and e.g. further instructions (e.g. for administration) and e.g. further means for injection. In a preferred embodiment, an injection pen for multiple injections is used, whereby the gonadotropin solution is filled in respective cartridges. The active ingredients can be in different cartridges, but can of course be injected simultaneously, or in sequential order, as is well known to the person skilled in the art. Also, two or more active ingredients can be within one and the same cartridge.

In a very preferred embodiment, the present formulation is for parenteral use, even more preferred for subcutaneous injection.

In a preferred embodiment, the hMG is present in the formulation in an amount of 35-850 IU/ml, preferably 50-800 IU/ml, even more preferred 100-700 IU/ml, most preferred 625 IU/ml, typically in a multidose formulation.

A particularly preferred formulation of excipients for a multidose formulation comprising hMG as above, and/or comprising hMG, and/or hCG, and/or all other gonadotropins as mentioned as coming under the present invention, has the following composition:
50-160 mM arginine HCl, preferably 150 mM, arginine HCl
0.05 to 1.5 mg/ml, preferably 0.15 mg/ml, L-methionine
0.001-0.05 mg/ml, preferably 0.005 mg/ml, Polysorbate 20
4.0 to 6.0 mg/ml, preferably 5.0 mg/ml, phenol
pH 6.0 to 7.5, preferably pH 6.8+/−0.3, (the pH refers to the pH of the whole solution.) WFI.

Typical concentrations of the active ingredient for formulations comprising recombinant hCG and/or FSH are as follows, although the concentration of the active ingredient does not have any influence on the performance of the present invention:
For rFSH: 30-150 µg/ml
For rhCG: 5-200 µg/ml The preferred excipients for such recombinant formulations are the same as described above for the multidose hMG formulation. Typical single-dose formulations are also encompassed in this invention and would be the same as described above with the exception that they would not comprise a preservative, like phenol.

Injectable depot forms can be made by forming micro encapsulated matrices of the gonadotropin (and other agents, if present) in biodegradable polymers. The polymer based depot forms/sustained release systems can, dependent on their chemical nature, be for example micro- or nanoparticles, hydrogels, micelles, emulsions or implants. Depending upon the ratio of gonadotropin to polymer and the nature of the particular polymer employed, the rate of gonadotropin release can be controlled. Examples of biodegradable polymers include polylactide/polyglycolide copolymer systems, polyvinylpyrrolidone, poly(orthoesters), poly(anhydrides), poly(ethylene glycol), poly amino acids, polysaccharides e.g. sodium hyaluronate (NaHA) or other salts hereof, gelatin, chitosan etc. All mentioned polymers can be derivatized or modified to optimize the protein drug delivery or its stability. Depot injectable formulations are also prepared by entrapping the gonadotropin in lipid systems, or polymer lipid mixtures as micelles, liposomes or micro-emulsions which are compatible with body tissues.

Injectable formulations can be sterilized, for example, by filtration through a bacterial-retaining filter, and/or by incorporating sterilizing agents. It is possible to form sterile solid compositions which can be dissolved or dispersed in sterile water or other sterile injectable medium just prior to use. Injectable formulations can be supplied in any suitable container, e.g. vial, pre-filled syringe, injection cartridges, and the like, as described above.

The pH and exact concentration of the various components of a formulation for use as a pharmaceutical composition as described herein are principally adjusted in accordance with routine practice in this field, see e.g. The textbook of Pharmaceutical Medicine, fifth edition, edited by John P. Griffin and John O'Grady. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

The FSH, hCG and/or LH that can be formulated in accordance with the present invention can be derived by conventional means from urine, as is well known in the art, or can be produced recombinantly. For possible production methods it is further referred to e.g. WO 2009/127826.

One preferred embodiment of the invention is the presently described formulation comprising hCG.

hCG can be obtained by any means known in the art. hCG as used herein includes urinary-derived hCG and recombinant hCG. A formulation comprising urinary derived hCG is particularly preferred. A formulation having LH activity which is—at least partly—derived from hCG (in other words: the hCG is the molecule which is responsible for this LH activity) is also encompassed. Human-derived hCG can be purified from any appropriate source (e.g. urine and/or placenta) by any method known in the art. Methods of expressing and purifying recombinant hCG are well known in the art.

LH can be obtained by any means known in the art. LH, as used herein, includes human-derived LH and recombinant LH. Human-derived LH can be purified from any appropriate source (e.g. urine) by any method known in the art. Methods of expressing and purifying recombinant LH are known in the art.

The term "pharmaceutical composition" is used herein interchangeably with "pharmaceutical formulation".

The stable pharmaceutical composition of the present invention may be used for the treatment of infertility. "Treatment of infertility" in the context of this invention includes treatment of infertility by controlled ovarian (hyper)stimulation (COS) or methods which include a step or stage of controlled ovarian stimulation, for example Intra Uterine Insemination (IUI), in vitro fertilisation (IVF), or intracytoplasmic sperm injection (ICSI). The term also includes ovulation induction (OI) or methods which include a step or stage of ovulation induction. The term also includes treatment of infertility in a subject having tubal or unexplained infertility, including treatment of infertility in a subject having endometriosis, for example stage I or stage II endometriosis (as defined by the American Society for Reproductive Medicine (ASRM) classification system for the various stages of endometriosis, Revised American Society for Reproductive Medicine classification of endometriosis: 1996, Fertil Steril 1997; 67, 817-821), and/or in a subject with a partner with male factor infertility. The term preferably includes the use in e.g. assisted reproductive technologies (ARTs), ovulation induction (OI) or intrauterine insemination (IUI). The pharmaceutical composition may be used, for example, in medical indications where known FSH preparations or preparations of FSH and hCG are used. In a typical embodiment, the present formulation is used for the same medical indications as those indications approved for Menopur®, in Europe, as follows, in an exemplary case:

Treatment of Female and Male Infertility:
  Anovulatory women: MENOPUR can be used to stimulate follicle development in amenorrhoeic patients. Clomiphene (or a similar ovulation inducing agent which influences steroid feed-back mechanisms) is the preferred treatment for women with a variety of menstrual cycle disturbances, including luteal phase insufficiency with anovulatory cycles and with normal prolactin, and also amenorrhoeic patients with evidence of endogenous oestrogen production but normal prolactin and normal gonadotropin levels. Non-responders may then be selected for menotrophin therapy.
  Women undergoing superovulation within a medically assisted fertilisation programme: MENOPUR can be used to induce multiple follicular development in patients undergoing an assisted conception technique such as in-vitro fertilisation (IVF).

Hypogonadotrophic hypogonadism in men: MENOPUR may be given in combination with human chorionic gonadotropin (e.g. Choragon) for the stimulation of spermatogenesis.

or the indications as approved for Menopur® in the US as follows:

Development of multiple follicles and pregnancy in ovulatory women as part of an Assisted Reproductive Technology (ART) cycle.

Alternatively, the treatment options with Menopur® can be described as follows:

MENOPUR is indicated for the treatment of infertility in the following clinical situations: Anovulation, including polycystic ovarian disease (PCOD), in women who have been unresponsive to treatment with clomiphene citrate.

Controlled ovarian hyperstimulation to induce the development of multiple follicles for assisted reproductive technologies (ART) (e.g. in vitro fertilisation/embryo transfer (IVF/ET), gamete intra-fallopian transfer (GIFT) and intra-cytoplasmic sperm injection (ICSI)).

Stimulation of follicular development in women with hypogonadotrophic hypogonadism.

The present invention also provides the use of the stabilized gonadotropin formulations described herein (according to aspects of the invention) for, or in the manufacture of a medicament for, the treatment of infertility.

In a preferred embodiment the present inventive formulation is used for ovulation induction, assisted reproductive techniques (ART) and/or for hypogonadotrophic hypogonadism in men.

The pharmaceutical compositions can be further formulated into well-known compositions for any route of drug administration, e.g. oral, rectal, parenteral, transdermal (e.g. patch technology), intravenous, intramuscular, subcutaneous, intracisternal, intravaginal, intraperitoneal, local (powders, ointments or drops) or as a buccal or nasal spray. A typical composition comprises a pharmaceutically acceptable carrier, such as aqueous solution, non-toxic excipients, including salts and preservatives, buffers and the like, as described in Remington's Pharmaceutical Sciences fifteenth edition (Matt Publishing Company, 1975), at pages 1405 to 1412 and 1461 to 87; and USP-NF, The National Formulary XIV fourteenth edition (American Pharmaceutical Association, 1975), among others. The present invention is directed in some embodiments to the specific provision of a formulation which exhibits both surprisingly high stability and further advantages, like no unacceptable coloring, no unacceptable turbidity, reduced or no pain upon injection, and reduced or no skin irritation upon injection. This has become possible only with the findings of the present invention which shows that particular components enable the advantageous performance and high stability of the liquid gonadotropin formulations described herein.

Although gonadotropin formulations have been on the market for several decades now, the formulation scientist is well aware that the formulation of these proteins is associated with a number of difficulties. These difficulties exist and vary severely on the basis on many factors, like The fact that a protein is being formulated (proteins as such are difficult to formulate in any case)

The fact that the protein is specifically glycosylated (glycosylation might be influenced by the specific selection of the manufacturing and the excipients)

The specific protein(s) formulated (formulation chemistry varies significantly depending on the actual protein: it has e.g. been shown that even closely related proteins like FSH and hCG behave differently in the same formulation, see e.g. WO 2012/013742)

Whether or not the protein was obtained from nature, e.g. urine, or produced recombinantly Whether a preservative is needed (some preservatives fulfill their intended goal of protection against microbial growth, but affect the stability of the final formulation negatively. This is true for all of m-cresol, phenol and benzyl alcohol (with or without benzalkonium chloride), which are currently the only preservatives authorized for use with gonadotropins; in addition, preservatives can have a negative effect on coloring, depending on the further excipients and active ingredient comprised in the formulation)

The specific surface-active agent used (these might in some instances lead to turbidity, again depending on the further excipients as comprised in a respective formulation)

The specific buffer used (e.g. citrate buffer will frequently lead to pain and skin irritation upon injection)

The specific excipients used for stabilization, which will stabilize different compositions in unpredictable ways.

Depending on the excipient used for stabilization which will stabilize different compositions in unpredictable ways.

Thus, the formulation scientist is faced with a set of multiple problems on the one hand and a set of a multitude of possible excipients on the other hand, leading to a complex problem for providing a formulation with a good stability on the one hand and no coloring or turbidity or pain upon injection on the other hand.

It was quite surprising, therefore, that the present combination of arginine and methionine, without the addition of buffer solved these particular problems, in the present pH range.

In this regard, "without (the addition of/an additional) buffer" and "does not comprise a buffer" is used synonymously in this application. This expression shall mean that no additional compound is added/present in the formulation that would be considered to have buffer capacity. A solution is said to be buffered if it resists changes in the activity of an ion on the addition of substances that are expected to change the activity of that ion. Buffers are substances or combinations of substances that impart this resistance to a solution. Buffered solutions are systems in which the ion is in equilibrium with substances capable of removing or releasing the ion. It refers to the amount of material that may be added to a solution without causing a significant change in ion activity. It is defined as the ratio of acid or base added (in gram-equivalents/L) to the change in pH units. The capacity of a buffered solution is adjusted to the conditions of use, usually by adjustment of the concentrations of buffer substances (USP NF). Buffer capacity is expressed commonly as the number of equivalents (Eq) of strong acid (e.g. HCl) or base (e.g. NaOH) that causes one liter of the solution in question to undergo one unit change in pH (preferably at one atmosphere and 21° C.) (Skoog West and Holler, Fundamentals of Analytical Chemistry, fifth edition). One equivalent HCl is equal to one mole HCl and one equivalent NaOH is equal to one mole NaOH. In the present invention the buffer capacity will be expressed as number of equivalents (Eq) of strong acid (e.g. HCl) or base (e.g. NaOH) that causes one liter of the solution in question to undergo one unit change in pH. Thus, in accordance with the present invention, the formulation shall not comprise an additional buffer, that contributes with ≥0.5 mEq/(liter*pH)(preferably at 1 atm, 21° C.) in the pH range as disclosed for the present inventive formulations.

Method to Determine and Calculate Buffer Capacity

Buffer capacity can be determined and calculated as follows.

A definite volume of the solution to be tested is titrated with acid e.g. HCl or base e.g. NaOH. Suitable concentrations of acid and base e.g. 0.2 N should be used to make a sufficiently precise titration.

Titration is performed by adding small aliquots of HCl or NaOH to the test solution. For each addition the added volume and the corresponding pH is documented.

The accumulated volume of acid and base is plotted against the measured pH, see e.g. FIG. 1.

A linear least square regression fit is performed for the relevant pH area and $R^2$ s calculated to confirm the validity of the fitted line.

The buffer capacity expressed in mEq/(litre×pH unit) is calculated by linear regression.

$$Y = ax + b \Leftrightarrow x = \frac{Y-b}{a} \qquad \text{Equation 1}$$

where;
x=Buffer capacity [μL 0.2 N HCl/NaOH to move pH 1 pH unit]
Y−b=1 pH unit
a=Slope
and $$x = \frac{(Y-b) \times C}{a \times V \times 10^6} \qquad \text{Equation 2}$$

Where mEq is milliequivalents of acid or base is given from the concentration e.g. 0.2 N HCl/NaOH which is equal to 0.2 equivalents/L HCl/NaOH which is equal to 200 mEq/L HCl/NaOH.

$x$ = Buffer capacity [mEq/litre × pH unit]

$Y-b$ = 1 pH unit $C$ = Concentration of acid or base e.g. for HCl/NaOH $\left[\frac{mmol}{L} = \frac{mEq}{L}\right]$ $V$ = Volume of solution in question $10^6$ correction factor from μL to litre Example of calculation using Equation 2 and batch C-01$_{pH\ range\ 6.564\text{-}6.947}$, from table 9:

$$x = \frac{1 \times 200}{0.001507 \times 0.1 \times 1000000} = 1.32 \text{ mEq/(litre} \times \text{pH unit)}$$

To determine if a component will contribute with ≥0.5 mEq/(litre×pH unit) to the buffer capacity, the buffer capacity is determined as described above for a solution with the component and for the same solution without the component. The difference in the determined buffer capacity for the two solutions gives the contribution of the given component to the buffer capacity.

The terms "without (the addition of/an additional) buffer" and "does not comprise a buffer" also means that the present inventive formulation does not comprise any one of the following buffers, (which are FDA approved buffers for parenteral use in the range of pH 6.0-7.5):
Histidine
Phosphate
Citrate
Trometamine (Tris)
Hydroxyethylpiperazine Ethane Sulfonic Acid (HEPES)
Carbonate Additionally, the terms also mean that none of the further FDA approved buffers for parenteral use is included, in particular
Acetate
Adipic acid
Ammonium sulphate
Succinate
Asparagine
Aspartic acid
Glutamate (Glutamic acid)
Glycine
Lactate
Lysine
Maleate (Maleic acid)
Fumarate (Fumaric acid)
Malate
Meglumine
Propionate
Alanine
Phenylalanine
Cysteine
Isoleucine
Leucine
Proline
Serine
Tartrate
Threonine
Tryptophan
Tyrosine
Valine Without the addition of a buffer it is usually assumed that the pH of the final solution cannot be kept easily in the desired range (and it will be difficult to reach a specific target pH during adjustment) (in the present invention, the pH should be between 6.0 and 7.5, more preferred between 6.5 and 7.4, preferably at or around 6.8), but will fluctuate severely.

It is extremely important to maintain the correct pH for a pharmaceutical product. The pH defines parameters like stability, activity and shelf life. For that reason, pharmaceutical formulations are usually formulated with a buffer. A variety of buffering agents is available and they are selected to be effective at the desired pH. Exemplary buffers which are used regularly in practically all existing gonadotropin formulations are phosphate buffer, and citrate buffer. The buffer needs to provide the formulation with a maintained pH over the range of conditions to which the formulation might be exposed during formulation and in particular during storage thereof. It is often quite challenging to find such a suitable buffer, and then in some cases an effective buffer provides the formulation with undesired side-effects, like pain upon injection for citrate buffers. All buffers have the inherent disadvantage of being an additional ingredient in the formulation which complicates the formulation process, poses a risk of deleteriously affecting other ingredients, stability, shelf-life, and acceptability to the end user.

The present inventors, however, surprisingly have provided formulations where no buffer is present, while the formulations do not suffer from any unacceptable pH fluctuation. The formulations comprise arginine as a stabilizing compound. Arginine would have an expected buffering capacity of +/−1 pH units around its pKa, which is at 2.17, at 12.5 and at 9.04. Thus, no buffering capacity was expected at the preferred pH range of this invention (e.g., between 6.0 and 7.5, more preferred between 6.5 and 7.4, preferably at or around 6.8). Nevertheless, it was surprisingly discovered that arginine has a strong stabilizing influence on the pH in the particular formulations described herein. No such effect of arginine has been described anywhere in the prior art.

Advantageously, the provision of this formulation without a buffer as defined herein also provides a formulation with reduced or no pain upon injection and reduced or no skin irritation upon injection. This is contrary to formulations which e.g. use citrate buffer which has been shown to lead to skin irritation and pain upon injection.

The arginine of this invention can be arginine, or can be arginine HCl, or even more preferred, L-arginine (HCl). The amount of arginine is preferably in the range between 50 and 160 mM, more preferred 80-160 mM, even more preferred at approx. 150 mM.

As can be seen from the examples below, arginine has a pronounced effect on oxidation of FSH and hCG. However, the inventors did show a particularly high stabilizing effect. Quite surprisingly, they were then able to provide a liquid gonadotropin formulation which was stable and showed only minimal oxidation (in acceptable levels, see example section below), if the gonadotropin was combined with a high stabilizing amount of arginine (e.g. 150 mM).

This was particularly surprising as the effect was obtained in a pH range far removed from the pKa values of arginine, namely in a pH range of pH 6.0 to 7.5. This is the preferred pH range for the present invention. In a particularly preferred embodiment, the pH is in the range of 6.5 to 7.4. Even more preferred is a pH range between 6.5 and 7.2. Most preferred is a pH of 6.8+/−0.3.

Surprisingly, a low anti-oxidant amount of methionine, preferably L-methionine, was able to prevent undesirable oxidation events. This low amount could be as low as 0.05 mg/ml, but could go up to 2.5 mg/ml. In a preferred embodiment, the amount of methionine is between 0.1 and 1.5 mg/ml. In an even more preferred embodiment the amount of methionine is between 0.1 and 1 mg/ml. In an even more preferred embodiment, the amount of methionine is between 0.1 and 0.5 mg/ml. The most preferred embodiment is methionine at 0.15 mg/ml. It could not have been predicted at all that the high oxidation power of arginine could have been countered and overcome by such a low amount of methionine.

Even further surprising was the finding that arginine had a much more pronounced stabilizing effect than other known stabilizing agents, e.g. sucrose, which is a stabilizer quite frequently added and very well established.

The formulations may include suitable aqueous and non-aqueous pharmaceutical carriers, diluents, solvents and/or vehicles. Examples of suitable aqueous and non-aqueous pharmaceutical carriers, diluents, solvents or vehicles include water, ethanol, polyols (such as glycerol, propylene glycol, polyethylene glycol, and the like), carboxy-methyl-cellulose and suitable mixtures thereof, vegetable oils (such as olive oil), and injectable organic esters such as ethyl oleate.

Further preferred, especially for multidose formulations, in the present invention is the addition of a preservative. Very preferred this preservative is phenol. In a further preferred embodiment, the phenol is added at a concentration of 4.0 to 6.0 mg/ml, preferably 5.0 mg/ml phenol. Surprisingly, the phenol is also advantageous in the context of the specific present formulation, compared to other well known preservatives, in that it does not lead to a coloring and is very stable, even over a prolonged time period, in spite of the presences of this preservative, as shown in the example section.

Further preferred in the present invention is the addition of a surface active agent. Very preferred this surfactant is a polysorbate, even more preferred polysorbate 20. In a further preferred embodiment, the polysorbate 20 is added at a concentration of 0.001-0.05 mg/ml, preferably 0.005 mg/ml Polysorbate 20. Advantageously, the formulation of this invention, compounded with polysorbate 20, does not lead to turbidity and is very stable, even over a prolonged time period, in spite of the presence of this preservative, as shown in the example section.

The compositions can also contain further additives in addition to those already listed above, such as but not limited to (further) preservatives, wetting agents, emulsifying agents, and dispersing agents. Antibacterial and antifungal agents can be included to prevent growth of microbes and includes, for example, parabens, chlorobutanol, phenols, sorbic acid, and the like. Furthermore, it may be desirable to include tonicity agents. The present inventive formulation however does not comprise an additional buffer.

In some cases, to effect prolonged action, it is desirable to slow the absorption of the gonadotrophin(s) such as FSH (and other active ingredients, if present) from subcutaneous or intramuscular injection. This can be accomplished by the use of a liquid suspension of crystalline or amorphous material with poor water solubility. The rate of absorption then depends upon the rate of dissolution which, in turn, can depend upon crystal size and crystalline form. Alternatively, delayed absorption of a parenterally administered FSH combination form is accomplished by dissolving or suspending the FSH combination in an oil vehicle.

According to the present invention, an effort was made by the inventors to investigate the effect of certain compounds on the stability of a liquid gonadotropin formulation; here, stabilizing as well as destabilizing effects of several compounds were investigated. Additionally, the inventors sought to improve the resultant formulation as to its clarity, degree of coloration, and pain upon injection.

The term "stability" can refer to chemical stability, involving covalent modification in the amino acid sequence, but in the context of protein stability it can also refer to physical stability, which involves changes of the protein folded state (i.e. the native state) not including covalent bond cleavage. In the present invention the term "stability" refers to the bio-stability of formulations of gonadotropins, in particular FSH and hCG. Physical instability of a protein formulation may be caused by aggregation of the protein molecules to form higher order aggregates, by dissociation of the heterodimers into monomers, or by any other conformational change that reduces at least one biological activity of e.g., FSH proteins (and other active ingredients, if present) included in the present invention.

A "stable" solution or formulation is one wherein the degree of, aggregation, dissociation, conformational modification, loss of biological activity and the like, of proteins therein is acceptably controlled, and does not increase unacceptably with time. Stability may be assessed by methods well-known in the art, including measurement of a sample's light scattering, visual inspection of clarity and/or coloration, absorbance, or optical density, molecular size determinations (e.g. by size exclusion chromatography or field flow fractionation), in vitro or in vivo biological activity and/or by differential scanning calorimetry (DSC).

The present formulation is stable for 12 months at storage conditions, preferably 16 months at storage conditions, even more preferred for 24 months, even more preferably for 24 months at storage conditions plus 1 month "in use", i.e. at room temperature. Stability at "storage conditions" refers to storage of the formulation in a cooled environment, e.g. at 5° C.±3° C. "Room temperature" in the present context is meant to refer to at or below 30° C., preferably 15-25° C., preferably 18-25° C., most preferred 25±2° C.

To determine stability in the context of the present formulation well known (immuno)assays for FSH and hCG were used, which are well known to the person skilled in the art and described herein consequently only in general terms as follows:

RP-HPLC for Oxidation

Oxidization of proteins was determined by RP-HPLC, by gradient elution on a C4 column and UV detection at 210 nm.

Enzyme-Linked Fluorescent Assay (ELFA)

The immunoactivity of FSH and hCG was determined in a sandwich immunoassay performed using an automatic analyser VIDAS® instrument (BioMérieux, France) with VIDAS® kits corresponding to FSH and hCG, respectively.

Size Exclusion Chromatography (SEC)

Purity of rFSH was determined with size exclusion chromatography (SEC) on an SEC column with protein range 3-70 kDa and UV detection at 210 nm.

Hydrophobic Interaction Chromatography (HIC)

Purity of rhCG was determined with hydrophobic interaction chromatography (HIC) by gradient elution on a column with alkyl amide groups and UV detection at 220 nm.

FSH and LH Bioassay

FSH and LH potency were determined using biological in vivo assays; Steelman-Pohley (FSH) and seminal vesicle weight gain assay (LH), respectively.

Other methods for assessing stability are well known in the art and can also be used according to the present invention.

The FSH and LH activity assays are standardized using the Fourth International Standard for Urinary FSH and Urinary LH, November 2000, by the Expert Committee on Biological Standardization of the World Health Organization (WHO ECBS) and are well known to the person skilled in the art.

It was known that several preservatives have a pronounced destabilizing effect on gonadotropin formulations and it was found surprisingly here that the described inventive formulation, in particular comprising arginine and methionine, but not buffer, was particularly stable—even over a prolonged time period and even in the presence of phenol.

The presently claimed combination of arginine and methionine has a stabilizing effect on a liquid hMG formulation which is in an advantageous and surprising manner even more pronounced than the stabilizing effects of known stabilizers, like e.g. sucrose. The improved stabilization effect compared to the known stabilizers like sucrose is particularly surprising. Further, quite unexpected, the stabilizing effects of the inventive combination was pronounced in spite of the absence of a buffer.

It has been known from the prior art that there is degradation of FSH occurring in pharmaceutical FSH formulations and this has been confirmed by examples provided in WO 2012/013742. FSH will degrade both as a function of time as well as a function of temperature.

It appears that the conformational unfolding of tertiary and secondary FSH structures occurring upon heating is a two-state transition (when protein aggregation is limited). This unfolding may be independent of subunit dissociation (changes in the quaternary structure).

Further, it became clear in the prior art that FSH, containing a preservative like benzyl alcohol or phenol, where such preservatives are necessary, for example as antimicrobial agents in liquid FSH formulations, clearly affect the stability of FSH multidose formulations in a negative manner. Here, the long term stability of FSH is decreased, the denaturation temperature of FSH is lower, and the already denatured forms have a lower level of secondary structures than FSH formulations not containing preservatives.

The present invention also pertains to a method for stabilization of a liquid gonadotropin formulation wherein the method comprises the step of an addition of arginine and methionine to said formulation, which does not comprise a buffer.

LIST OF FIGURES

FIG. 1: Titration curve. The slope of the curves shows the buffer capacity, e.g. a steep slope depicts a low buffer capacity.

Figure 2:
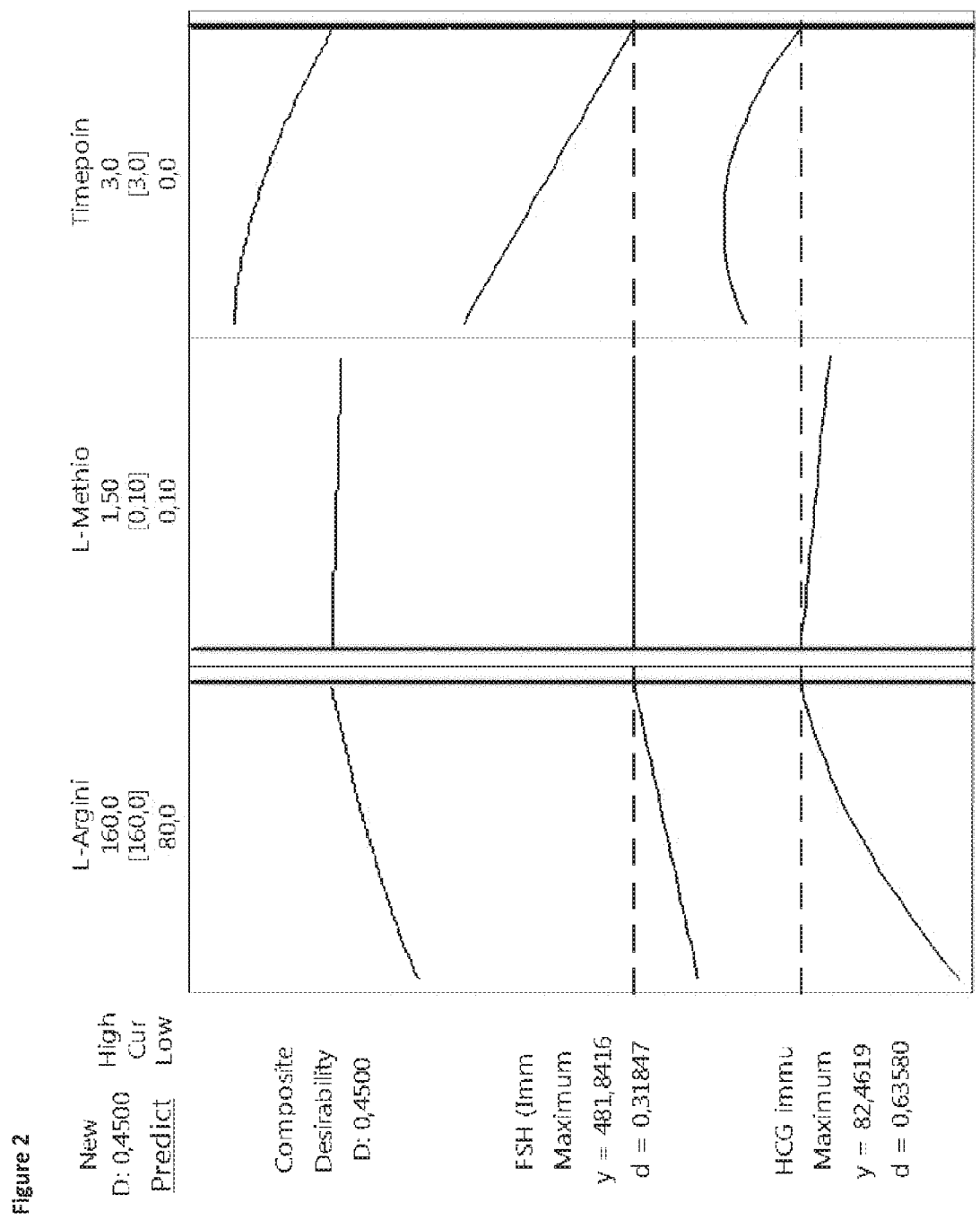

FIG. 2: Response optimizer based on 25° C. results. Vertical lines show the level of L-arginine and L-methionine and the responses in the FSH and hCG immunoassay as Y (in IU/ml). $R^2_{HCG}$: 92.15% and $R^2_{FSH}$: 67.31%.

All studies were confirmed by the additionally conducted real-time data.

EXAMPLES

Example 1

1 Background and Introduction

Several different drug products containing gonadotropin hormones derived from urine of postmenopausal or pregnant women are used in the treatment of infertility, such as hMG (human menopausal gonadotropin) preparations. hMG possess Follicle Stimulating Hormone (FSH) and Luteinizing Hormone (LH) activity in a one to one ratio.

FSH, LH and human chorionic gonadotropin (hCG) belong to the gonadotropins family of complex glycoprotein hormones. They are heterodimers composed of an α- and a β-subunit. The 92 amino acid α-subunit is common for these three gonadotropins, the β-subunits are unique, giving them their different biological characteristics (Wolfenson C. et al. 2005, Batch-to-batch consistency of human-derived gonadotropin preparations compared with recombinant preparations. *Reproductive BioMedicine*. Vol 10 No. 4:442-454; Shen, S. T., Cheng, Y. S., Shen, T. Y., and Yu, J. Y. 2006, Molecular cloning of follicle-stimulating hormone (FSH)-beta subunit cDNA from duck pituitary. *Gen. Comp Endocrinol*. 148:388-394; Fox, K. M., Dias, J. A., and Van, R. P. 2001, Three-dimensional structure of human follicle-stimulating hormone. *Mol. Endocrinol*. 15:378-389; Burova, T., Lecompte, F., Galet, C., Monsallier, F., Delpech, S., Haertle, T., and Combarnous, Y. 2001, Conformational stability and in vitro bioactivity of porcine luteinizing hormone. *Mol. Cell Endocrinol*. 176:129-134. The glycoprotein hormones all lose their bioactivity upon dissociation of the non-covalently linked subunits (Alevizaki, M. and Huhtaniemi, I. 2002, Structure-function relationships of glycoprotein hormones; lessons from mutations and polymorphisms of the thyrotrophin and gonadotropin subunit genes. *Hormones*. (Athens.) 1:224-232).

LH and hCG binds to the same receptor and therefore both possess LH activity. In hMG the LH activity is originating mostly from hCG.

It is the goal of the present invention to develop a gonadotropin formulation as a liquid formulation, for subcutaneous injection. For multidose injection, addition of a preservative typically is necessary (Meyer, B. K., Ni, A., Hu, B., and Shi, L. 2007, Antimicrobial preservative use in parenteral products: past and present. *J. Pharm. Sci.* 96:3155-3167; Chang, B. S. and Hershenson, S. Practical Approaches to Protein Formulation Development. In Rational Design of Stable Protein Formulations. J. F. Carpenter and M. C. Manning, editors. 2002, Plenum Publ., New York. 1-25; Pharmaceutical Formulation Development of Peptides and Proteins. 2000, CRC Press, Boca Raton).

As in general, the native (bioactive) structure of proteins is very sensitive towards its surroundings e.g. the composition of the formulation, the container/closure systems, pH and temperature it is a difficult feat to identify a suitable liquid formulation for gonadotropins, different excipients were screened. In the present work the buffer capacity and real time stability of various hMG formulations are investigated using an FSH immunoassay, an hCG immunoassay, a bioassay, RP-HPLC for determination of oxidized proteins, titration and pH as described below in detail.

2 Product to be Studied

2.1 Materials

2.1.1 Drug Substance (DS)

The hMG-HP drug substance (DS) was manufactured by Instituto Massone S. A. Argentina hMG-HP DS is received as a powder by Ferring Pharmaceuticals A/S, Copenhagen, Denmark.

Determination of FSH and LH biological activity in the drug substance was performed according to the current version of the British Pharmacopeia (BP). It is also possible, if desired, to carry out this determination according to the USP 35 version. The FSH:LH bioactivity in hMG is 1:1 and therefore the average determined bioactivity of FSH and LH is used for compounding to drug product. Hence, when the concentration of hMG is given as e.g. 625 IU/ml it equals a bioactivity of 625 IU/ml FSH and 625 IU/ml LH.

2.1.2 Excipients

A list of the excipients used in this work is described in Table 1.

TABLE 1

| List of excipients | | |
| --- | --- | --- |
| Name | Quality | Manufacturer |
| Sodium hydroxide pellets | Ph Eur, BP, JP, NF | Merck |
| Hydrochloric acid, fuming 37% | Ph Eur, BP, JP, NF | Merck |
| Citric acid Monohydrate | Ph Eur, BP, JPE, USP | Merck |
| ortho-Phosphoric acid 85% | Ph Eur, BP, JPE, NF | Merck |
| Tri-sodium citrate dihydrate | Ph Eur, BP, JPE, USP | Merck |

TABLE 1-continued

| List of excipients | | |
| --- | --- | --- |
| Name | Quality | Manufacturer |
| Di-sodium hydrogen phosphate dodecahydrate | Ph Eur, BP, JPE, USP | Merck |
| L-histidine | EMPROVE ® exp Ph Eur, USP | Merck |
| L-methionine | USP, multicompendial | J.T. Baker |
| L-arginine | Ph Eur, USP | Merck |
| L-arginine monohydrochloride | Pharma Grade, EP, JP, USP | Sigma-Aldrich |
| Sucrose | EMPROVE ® exp Ph. Eur, BP, JPE, NF | Merck |
| D-(+)-trehalose dehydrate | ≥99%, cGMP | Sigma-Aldrich |
| Mannitol | EMPROVE ® Ph Eur, BP, USP, JPE | Merck |
| Lactose monohydrate | Ph Eur, BP, NF, JP | Merck |
| Glycine | EMPROVE ® Ph. Eur., BP, JPE, USP | Merck |
| Sodium Chloride | EMPROVE, Ph. Eur., BP, USP | Merck |
| Polysorbate 20 | Ph. Eur, NF, JPE | J.T. Baker |
| Poloxamer 188 | Suitable for bio. Pharm. Production, Ph. Eur., NF | Merck |
| Phenol | Ph. Eur, JP, USP | Merck |
| Meta-cresol | Ph. Eur./USP parenteral grade | Hedinger |
| Milli-Q water | — | Millipore |

2.1.3 Container Closure System

For the stability studies, the primary packing materials were glass vials with rubber stoppers and alu/plastic caps, or glass cartridges with rubber plungers and crimp caps.

3 Manufacturing Procedure

3.1 Compounding

All formulations are manufactured at lab-scale.

For compounding of drug product solution (DP), stock solutions of each excipient and drug substance (DS) are mixed sequentially. Before adding hMG and final dilution to volume, the pH of each formulation is adjusted, when necessary. Stock solutions of all excipients and hMG are prepared in Milli-Q water.

3.2 Sterile Filtration and Aseptic Filling

The formulations for stability are sterile filtered with Millipore PVDF 0.22 μm filter. Sterile filtration is performed in a LAF bench using autoclaved materials.

The filling is performed after filtration. The containers are filled with sample solution. All vials and cartridges are filled under aseptic like conditions in a LAF bench and immediately closed with rubber stoppers or crimp caps. Outside the LAF bench the filled vials are sealed with aluminium flip-off caps.

4 Storage Conditions

4.1 Storage Conditions

Containers containing drug product formulations are stored at accelerated conditions for up to 3 months at 30±2° C./65±5% RH and/or for up to a minimum of 6 months at 25±2° C./60±5% RH. At each storage temperature, the containers are stored in vertical positions. Cartridges are stored horizontally. All containers are protected from light.

5 Analytical Methods

The analytical methods used in the studies are described below.

5.1 Titration Procedure

According to USP-NF as described previously, a solution is said to be buffered if it resists changes in the activity of an ion on the addition of substances that are expected to change the activity of that ion. Buffers are substances or combinations of substances that impart this resistance to a solution. Buffered solutions are systems in which the ion is in equilibrium with substances capable of removing or releasing the ion. Buffer capacity refers to the amount of material that may be added to a solution without causing a significant change in ion activity. It is defined as the ratio of acid or base added (in gram-equivalents/L) to the change in pH units. The capacity of a buffered solution is adjusted to the conditions of use, usually by adjustment of the concentrations of buffer substances. Buffer capacity is expressed commonly as the number of equivalents (Eq) of strong acid or base that causes one liter of the solution in question to undergo one unit change in pH giving the unit mEq/(liter×pH) which was used for determination of the buffer capacity in the present invention. This means that the buffer capacity is defined as number of moles (equivalents) of $H^+/OH^-$ needed to change the pH of one liter buffer solution by one unit.

The buffer capacity was determined using placebo (placebo refers here to formulations without active ingredient) formulation adjusted to target pH as starting point. 0.2 N NaOH/HCl was used to titrate pH up or down. pH was measured after each addition of 0.2 N NaOH/HCl and the volume of 0.2 N NaOH/HCl was documented. The amount of 0.2 N NaOH/HCl was plotted as X-values and pH as Y-values. Fitted linear regression was performed around pH 6.8 for hMG placebo (target pH) and around pH 6.5 for reference placebo (target pH). The buffer capacity can be calculated as μL 0.2 N HCl/NaOH to move the pH by 0.01 pH unit/L DP and as milliequivalents (mEq) acid or base/(liter×pH unit), as described above in the definition.

5.2 FSH and hCG Immunoassay

The FSH and hCG immunoassay was determined by sandwich ELFA.

5.3 Oxidized Proteins

Oxidization of proteins was determined by RP-HPLC.

5.4 pH pH was measured according to Ph. Eur.

6 Results

The results of the stability studies, the evaluation of the buffering agent in a buffer capacity study, as well as the stability results from the Design of Experiment (DoE) study are presented below.

TABLE 2

Composition of liquid hMG (600 IU/ml) formulations

| Batch no. | Buffer | Surfactant | Preservative | Stabilizer/Tonicity agent |
|---|---|---|---|---|
| E-01 | 10 mM Phosphate[1] pH 6.8 | 0.005 mg/ml polysorbate 20 | 3.0 mg/ml M-cresol | 41.3 mg/ml Mannitol |
| E-02 | 10 mM Phosphate[1] pH 6.8 | 0.005 mg/ml polysorbate 20 | 3.0 mg/ml M-cresol | 85.9 mg/ml Trehalose |
| E-03 | 10 mM Phosphate[1] pH 6.8 | 0.1 mg/ml Poloxamer 188 | 3.0 mg/ml M-cresol | 74.3 mg/ml Sucrose |
| E-04 | 10 mM Phosphate[1] pH 6.8 | 0.1 mg/ml Poloxamer 188 | 3.0 mg/ml M-cresol | 18.8 mg/ml Glycine |
| E-05 | 10 mM Phosphate[1] pH 6.8 | 0.005 mg/ml polysorbate 20 | 5.0 mg/ml Phenol | 67.7 mg/ml Sucrose |
| E-06 | 10 mM Phosphate[1] pH 6.8 | 0.005 mg/ml polysorbate 20 | 5.0 mg/ml Phenol | 6.8 mg/ml NaCl |
| E-07 | 10 mM Phosphate[1] pH 6.8 | 0.1 mg/ml Poloxamer 188 | 5.0 mg/ml Phenol | 37.6 mg/ml Mannitol |
| E-08 | 10 mM Citrate[2] pH 6.8 | 0.005 mg/ml polysorbate 20 | 3.0 mg/ml M-cresol | 71.1 mg/ml Sucrose |
| E-09 | 10 mM Citrate[2] pH 6.8 | 0.005 mg/ml polysorbate 20 | 3.0 mg/ml M-cresol | 29.3 mg/ml L-arginine HCl |
| E-10 | 10 mM Citrate[2] pH 6.8 | 0.1 mg/ml Poloxamer 188 | 3.0 mg/ml M-cresol | 39.5 mg/ml Mannitol |
| E-11 | 10 mM Citrate[2] pH 6.8 | 0.005 mg/ml polysorbate 20 | 5.0 mg/ml Phenol | 74.7 mg/ml Trehalose |
| E-12 | 10 mM Citrate[2] pH 6.8 | 0.1 mg/ml Poloxamer 188 | 5.0 mg/ml Phenol | 64.5 mg/ml Sucrose |
| E-13 | 10 mM Citrate[2] pH 6.8 | 0.1 mg/ml Poloxamer 188 | 5.0 mg/ml Phenol | 6.5 mg/ml NaCl |
| E-14 | 10 mM Histidine pH 6.8 | 0.005 mg/ml polysorbate 20 | 3.0 mg/ml M-cresol | 77.5 mg/ml Sucrose |
| E-15 | 10 mM Histidine pH 6.8 | 0.1 mg/ml Poloxamer 188 | 3.0 mg/ml M-cresol | 19.6 mg/ml Glycine |

[1] 10 mM Di-sodium hydrogen phosphate dodecahydrate, pH adjusted with phosphoric acid
[2] 10 mM Tri-sodium citrate dihydrate, pH adjusted with citric acid

6.1 Stability of Liquid hMG Formulation/3 Months

Protein molecules can be stabilized by adding excipients to the solution e.g. salts, carbohydrates or amino acids but the degree of stabilization upon addition of different carbohydrates, salts and amino acids varies massively between different formulations. Here, the initial stability studies were performed to screen various stabilizers in combination with preservatives and buffers in a liquid formulation of hMG. Surprisingly, the results show a superior stabilizing effect of L-arginine as shown in Tables 3 and 6 for the hCG immunoassay and Tables 4 and 7 for the FSH immunoassay. Formulation E-09 exhibits a superior stability compared to all other formulations. Formulation E-09 is the only formulation which contains L-arginine (see Table 2). Formulation K-01, K-03 and K-04 as well as K-09 exhibit superior stability compared to all other formulations (see Table 6). These formulations again contain L-arginine (see Table 5). In Table 4, formulation E-09 excels with best stability compared to all other formulations also for the FSH immunoassay and Table 7 confirms that formulation K-09 shows the highest FSH immunoassay result compared to all other formulations.

TABLE 3 hCG immunoassay during 1 month storage at 30 ± 2° C./65 ± 5% RH. Formulation E-09 exhibits superior stability compared to all other formulations. Formulation E-09 contains L-arginine, see Table 2.

| Formulation | hCG [% of initial] Initial | 30° C. ± 2° C./65 ± 5% RH 0.5 month | 1 month |
|---|---|---|---|
| E-01 | 100 | 91 | 85 |
| E-02 | 100 | 88 | 87 |
| E-03 | 100 | 87 | 80 |
| E-04 | — | — | — |
| E-05 | 100 | 83 | 81 |
| E-06 | 100 | 101 | 100 |
| E-07 | 100 | 89 | 87 |
| E-08 | 100 | 89 | 81 |
| E-09 (L-arginine HCl) | 100 | 113 | 106 |
| E-10 | 100 | 95 | 91 |
| E-11 | 100 | 99 | 89 |
| E-12 | 100 | 94 | 87 |
| E-13 | 100 | 99 | 86 |
| E-14 | — | — | — |
| E-15 | — | — | — |

(Formulation E-04, E-14 and E-15 excluded from testing due to coloration)

TABLE 4

FSH immunoassay after 3 months storage at 30 ± 2° C./65 ± 5% RH. Formulation E-09 exhibits the best stability compared to all other formulations. Formulation E-09 contains L-arginine, see Table 2.

| Formulation | FSH [% of initial] Initial | 30° C. ± 2° C./65 ± 5% RH 3 months |
|---|---|---|
| E-01 | 100 | 83 |
| E-02 | 100 | 77 |
| E-03 | 100 | 83 |
| E-04 | — | — |
| E-05 | 100 | 84 |
| E-06 | 100 | 86 |
| E-07 | 100 | 86 |
| E-08 | 100 | 84 |
| E-09 (L-arginine) | 100 | 95 |
| E-10 | 100 | 83 |
| E-11 | 100 | 83 |
| E-12 | 100 | 89 |
| E-13 | 100 | 85 |
| E-14 | — | — |
| E-15 | — | — |

(Formulation E-04, E-14 and E-15 excluded from testing due to coloration)

6.2 Stability of Liquid hMG Formulation—3 Months
From initial screening additional formulations with arginine was screened.

TABLE 5

Composition stability study for liquid hMG 600 IU/ml-Overview of formulations

| Batch no. | Buffer | Surfactant | Preservative | Antioxidant | Stabilizer/ Tonicity agent |
|---|---|---|---|---|---|
| K-01[1] | 10 mM Citrate[5] pH 6.8 | 0.005 mg/ml Polysorbate 20 | 3.0 mg/ml M-cresol | 1.5 mg/ml L-methionine | 28.0 mg/ml L-arginine HCl |
| K-02 | 1 mM Phosphate[4] pH 6.8 | 0.005 mg/ml Polysorbate 20 | 3.0 mg/ml M-cresol | 1.0 mg/ml L-methionine | 21.0 mg/ml Lactose 7.0 mg/ml NaCl |
| K-03 | 10 mM Citrate[5] pH 6.8 | 0.1 mg/ml Poloxamer 188 | 5.0 mg/ml Phenol | 1.5 mg/ml L-methionine | 25.3 mg/ml L-arginine HCl |
| K-04 | 10 mM Phosphate[4] pH 6.8 | 0.005 mg/ml Polysorbate 20 | 3.0 mg/ml M-cresol | 1.5 mg/ml L-methionine | 29.3 mg/ml L-arginine HCl |
| K-05[2] | 10 mM Citrate[5] pH 6.8 | 0.1 mg/ml Poloxamer 188 | 5.0 mg/ml Phenol | 1.0 mg/ml L-methionine | 67.4 mg/ml Sucrose |
| K-06 | 10 mM Citrate[5] pH 6.8 | 0.1 mg/ml Poloxamer 188 | 3.0 mg/ml M-cresol | 1.0 mg/ml L-methionine | 74.6 mg/ml Sucrose |
| K-07[3] | 10 mM Citrate[5] pH 6.8 | 0.1 mg/ml Poloxamer 188 | 3.0 mg/ml M-cresol | 1.0 mg/ml L-methionine | 38.3 mg/ml Mannitol |
| K-08 | 10 mM Citrate[5] pH 6.8 | 0.1 mg/ml Poloxamer 188 | 5.0 mg/ml Phenol | 1.0 mg/ml L-methionine | 34.7 mg/ml Mannitol |
| K-09[6] | 10 mM Citrate[5] pH 6.8 | 0.1 mg/ml Poloxamer 188 | 3.0 mg/ml M-cresol | 1.5 mg/ml L-methionine | 20 mg/ml L-arginine HCl 22.1 mg/ml Sucrose |

[1] Same as formulation E-09 in table 2

[2] Same as formulation E-12 in table 2

[3] Same as formulation E-10 in table 2

[4] 10 mM Di-sodium hydrogen phosphate dodecahydrate, pH adjusted with phosphoric acid

[5] 10 mM Tri-sodium citrate dihydrate, pH adjusted with citric acid

[6] Strength is 530 IU/ml

TABLE 6 hCG immunoassay during 3 months storage at 25 ± 2° C./
60 ± 5% RH. Formulations K-01, K-03, K-04 and K-09 exhibit
superior stability compared to all other formulations. Formulation
K-01, K-03, K-04 and K-09 contain L-arginine, see Table 5

| hCG [% of initial] | | 25° C. ± 2° C./65 ± 5% RH | | |
|---|---|---|---|---|
| Formulation | Initial | 1 month | 2 months | 3 months |
| K-01 (L-arginine) | 100 | 110 | 105 | 105 |
| K-02 | 100 | 100 | 68 | 57 |
| K-03 (L-arginine) | 100 | 110 | 106 | 104 |
| K-04 (L-arginine) | 100 | 109 | 106 | 113 |
| K-05 | 100 | 94 | 82 | 71 |
| K-06 | 100 | 98 | 76 | 80 |
| K-07 | 100 | 85 | 74 | 67 |
| K-08 | 100 | 93 | 79 | 71 |
| K-09 (L-arginine) | 100 | 99 | 101 | 100 |

Very clearly, the formulations comprising L-arginine are much more stable than those comprising different stabilizing agents. Compare e.g. formulation K-02 and K-03 after three months.

TABLE 7

FSH immunoassay during 3 months storage at 25 ± 2° C./
60 ± 5% RH. Formulation K-09 show highest FSH
immunoassay result compared to all other formulations.
Formulation K-09 contains L-arginine, see Table 5

| FSH [% of initial] | | 25° C. ± 2° C./60 ± 5% RH | | |
|---|---|---|---|---|
| Formulation | Initial | 1 month | 2 months | 3 months |
| K-01 (L-arginine) | 100 | 112 | 112 | 111 |
| K-02 | 100 | 104 | 106 | 87 |
| K-03 (L-arginine) | 100 | 108 | 120 | 107 |
| K-04 (L-arginine) | 100 | 108 | 112 | 112 |
| K-05 | 100 | 107 | 116 | 111 |
| K-06 | 100 | 109 | 117 | 115 |
| K-07 | 100 | 101 | 112 | 104 |
| K-08 | 100 | 107 | 107 | 109 |
| K-09 (L-arginine) | 100 | 112 | 120 | 119 |

The results for hCG are also confirmed for FSH—compare e.g. formulation K-02 and K-03 after three months.

6.3 Buffer Capacity Study

Buffering agents e.g. sodium phosphate and sodium citrate are physiologically tolerated buffers and are quite commonly added to maintain the pH in a desired range. Tri-sodium citrate dihydrate and Di-sodium hydrogen phosphate dodecahydrate are evaluated as buffering agents by means of buffer capacity. The buffer capacity is calculated as the amount of acid or base needed to move the pH a predefined step, i.e. the amount of µL 0.2 N HCl/NaOH needed to move the pH by 1 pH unit/L DP calculated as mEq acid or base/(liter×pH unit) as explained above.

TABLE 8

Composition buffer capacity study-Overview Formulations

| Batch no. | Buffer | Surfactant | Preservative | Antioxidant | Stabilizer/ Tonicity agent |
|---|---|---|---|---|---|
| C-01 | No buffer pH 6.8 | 0.005 mg/ml Polysorbate 20 | 5.0 mg/ml Phenol | 1.5 mg/ml L-methionine | 120 mM L-arginine HCl[4] |
| C-02 | 5 mM Citrate[1] pH 6.8 | 0.005 mg/ml Polysorbate 20 | 5.0 mg/ml Phenol | 1.5 mg/ml L-methionine | 120 mM L-arginine HCl[4] |
| C-03 | 10 mM Citrate[1] pH 6.8 | 0.005 mg/ml Polysorbate 20 | 5.0 mg/ml Phenol | 1.5 mg/ml L-methionine | 120 mM L-arginine HCl[4] |
| C-04[3] | 1 mM[2] Phosphate pH 6.5 | 0.005 mg/ml Polysorbate 20 | 5.0 mg/ml Phenol | 1.0 mg/ml L-methionine | 31.76 mg/ml $Na_2SO_4 \times 10\ H_2O$ (14 mg/ml Sodium sulphate) |

[1] Tri-sodium citrate dihydrate
[2] 0.8 mM $Na_2HPO_4 \times 12\ H_2O$ and approx. 0.2 mM $H_3PO_4$ to pH 6.5
[3] Reference placebo
[4] Equal to 25.3 mg/ml L-arginine HCl The result of the titration conducted to determine buffer capacity is depicted in FIG. 1. The slope of the curves shows the buffer capacity, e.g. a steep slope represents a low buffer capacity. From FIG. 1 it can be observed that batch C-04 (reference formulation) has the lowest buffer capacity. In the relevant pH area 6.8±0.3 for hMG, all hMG formulations C-01 (no buffer), C-02 (5 mM Tri-sodium citrate dihydrate) and C-03 (10 mM Tri-sodium citrate dihydrate) have similar buffer capacity and a higher buffer capacity than the reference formulation containing 1 mM Di-sodium hydrogen phosphate dodecahydrate. The target pH for the reference formulation is 6.5. Formulation C-01, C-02 and -03 are compared with the reference which is known to have a stable pH. Numerous stability studies of the reference formulation C-04 have been conducted without any observed drifts in pH.

The following Table 9 shows the results of the buffer capacity study:

TABLE 9

Buffer capacity study. In the formulation relevant pH area 6.8 for hMG, all hMG formulations have a higher buffer capacity than the reference placebo formulation.

| Batch | Buffer | Buffer capacity around a target pH | pH range | α (slope) | Buffer capacity expressed as: mEq acid or base/(liter × pH unit) |
|---|---|---|---|---|---|
| C-01 | No buffer | 6.8 | 6.564-6.947 | 0.001507 | 1.32 |
| C-01 | No buffer | 7.0 | 6.786-7.193 | 0.000822 | 2.44 |
| C-02 | 5 mM Trisodium citrate dihydrate | 6.8 | 6.599-6.951 | 0.000672 | 2.96 |
| C-03 | 10 mM Trisodium citrate dihydrate | 6.8 | 6.572-6.946 | 0.000750 | 2.66 |
| C-04 (reference) | 1 mM Disodium hydrogen phosphate dodecahydrate | 6.5 | 6.199-6.752 | 0.002700 | 0.74 |
| C-04 (reference) | 1 mM Disodium hydrogen phosphate dodecahydrate | 6.8 | 6.582-6.982 | 0.002091 | 0.96 |

(C-01 and C-04 is mentioned twice because the buffer capacity was calculated in pH ranges around two different pH values respectively)

Surprisingly, the buffer capacity of the hMG formulation with no buffer (C-01) is higher than the reference formulation C-04. The main excipient component in the hMG formulation is L-arginine at a concentration of 120 mM. The pKa values for L-arginine are $pKa_1=2.17$; $pKa_2=9.04$ and $pKa_3=12.5$ (Handbook of Pharmaceutical Excipients. 2015, Pharmaceutical Press, London). It is very unexpected that arginine exhibits sufficient buffering behaviour far from the pKa values.

6.4 Oxidation Studies

After 3 months of storage at 30±2° C./65±5% RH, formulation E-09 containing L-arginine (see Table 5) has increased the level of oxidized proteins by 241% of the initial value (see table 10 below). This is a very high amount and there are instances where such high amounts of oxidation are not desirable.

Therefore, further studies were conducted to research whether this problem could be overcome.

There are several choices of antioxidants that can be used in protein formulations. Methionine can be added to prevent oxidation, by a proposed mechanism of competing with oxidation of the methionine residues in the proteins. The result of adding methionine to a formulation containing arginine is shown in Table 10. Formulation K-01, K-03, K-04 and K-09 contain arginine and methionine and the level of oxidized proteins is clearly and advantageously reduced. Formulation K-01 (with methionine) is the same formulation as formulation E-09 (without methionine). Comparing these two batches it can be seen that the level of oxidized proteins is reduced tremendously by methionine.

TABLE 10

Oxidized proteins % increase from initial during 3 months storage at 30 ± 2° C./65 ± 5% RH. Formulation E-09 contains arginine and no methionine. Formulation K-01, K-03, K-04 and K-09 contain arginine and methionine, see Table 5

| Oxidized proteins [% increase from initial] Formulation | 30° C. ± 2° C./ 65 ± 5% RH 3 months |
|---|---|
| E-01 | 44 |
| E-02 | 39 |
| E-03 | 47 |
| E-04 | — |
| E-05 | 37 |
| E-06 | 43 |
| E-07 | 36 |
| E-08 | 51 |
| E-09 (arginine and no methionine) | 241 |
| E-10 | 55 |
| E-11 | 47 |
| E-12 | 53 |
| E-13 | 46 |
| E-14 | — |
| E-15 | — |
| K-01 (arginine and methionine) | 24 |
| K-03 (arginine and methionine) | 12 |
| K-04 (arginine and methionine) | 8 |
| K-09 (arginine and methionine) | 13 |

(Formulation E-04, E-14 and E-15 excluded due to coloration)

In conclusion, these two studies demonstrate a tremendously stabilizing effect of arginine and an anti-oxidizing effect even of low amounts of methionine in a formulation of gonadotropins.

6.5 DoE Stability Study

Combining the results from the above studies, and the buffer capacity study, a DoE study was performed to investigate the interactions between arginine and methionine and to determine the optimal concentrations of these two excipients.

TABLE 11

Compositions for DoE stability study for liquid hMG 600 IU/ml-overview of formulations

| Batch no. | Buffer[2] | Surfactant | Preservative | Antioxidant | Stabilizer/ Isotonicity agent |
|---|---|---|---|---|---|
| D-01 | No buffer pH 6.8 | 0.005 mg/ml Polysorbate 20 | 5.0 mg/ml Phenol | 1.5 mg/ml L-methionine | 80 mM L-arginine HCl |
| D-02 | No buffer pH 6.8 | 0.005 mg/ml Polysorbate 20 | 5.0 mg/ml Phenol | 1.5 mg/ml L-methionine | 160 mM L-arginine HCl |
| D-03 | No buffer pH 6.8 | 0.005 mg/ml Polysorbate 20 | 5.0 mg/ml Phenol | 0.8 mg/ml L-methionine | 120 mM L-arginine HCl |
| D-04 | No buffer pH 6.8 | 0.005 mg/ml Polysorbate 20 | 5.0 mg/ml Phenol | 0.8 mg/ml L-methionine | 120 mM L-arginine HCl- |
| D-05 | No buffer pH 6.8 | 0.005 mg/ml Polysorbate 20 | 5.0 mg/ml Phenol | 0.1 mg/ml L-methionine | 160 mM L-arginine HCl |
| D-06 | No buffer pH 6.8 | 0.005 mg/ml Polysorbate 20 | 5.0 mg/ml Phenol | 0.1 mg/ml L-methionine | 80 mM L-arginine HCl |
| D-07[3] | No buffer pH 6.8 | 0.1 mg/ml Poloxamer 188 | 5.0 mg/ml Phenol | 1.5 mg/ L-methionine | 120 mM L-arginine HCl |
| D-08[3] | 10 mM Citrate[1] pH 6.8 | 0.1 mg/ml Poloxamer 188 | 5.0 mg/ml Phenol | 1.5 mg/ L-Methionine | 120 mM L-arginine HCl |

[1]Tri-sodium citrate dehydrate

[2]pH is adjusted with 0.2N HCl/NaOH for formulations without buffer and 0.2N NaOH/0.5M

[3]Citric acid Monohydrate for formulation with Tri-sodium citrate dihydrate buffer Included as reference formulations

6.5.1 FSH Immunoassay

Stability results of FSH immunoassay during storage for 3 months at 25±2° C./60±5% RH are listed in Table 12.

TABLE 12

Results of FSH immunoassay during storage at 25 ± 2° C./60 ± 5% RH. The full description of all formulations is listed in Table 11.

| FSH [IU/ml] | | 25° C. ± 2° C./60 ± 5% RH | | |
|---|---|---|---|---|
| Formulation | Initial | 1 month | 2 months | 3 months |
| D-01 | 516 | 501 | 468 | 462 |
| D-02 | 521 | 492 | 503 | 478 |
| D-03 | 511 | 503 | 513 | 474 |
| D-04 | 515 | 505 | 490 | 477 |
| D-05 | 532 | 521 | 513 | 473 |
| D-06 | 518 | 488 | 458 | 493 |
| D-07 | 518 | 528 | 482 | 490 |
| D-08 | 514 | 499 | 472 | 481 |

Statistical calculation was performed for FSH activity [IU/ml] to evaluate the influence and interaction of arginine and—methionine. The result of the statistical evaluation confirms that L-arginine has a statistical significant influence on FSH immunoassay stability results. Methionine has no statistical significant influence on FSH immunoassay stability results. There is no statistical significant interaction between arginine and methionine for this response parameter.

6.5.2 hCG Immunoassay

Stability results of hCG immunoassay during storage for 3 months at 25±2° C./60±5% RH are listed in Table 13 Table.

TABLE 13

Results of hCG immunoassay during storage at 25 ± 2° C./60 ± 5% RH. The full description of all formulations is listed in Table 11.

| hCG [IU/ml] | | 25° C. ± 2° C./60 ± 5% RH | | |
|---|---|---|---|---|
| Formulation | Initial | 1 month | 2 months | 3 months |
| D-01 | 83 | 82 | 75 | 56 |
| D-02 | 87 | 83 | 93 | 76 |
| D-03 | 93 | 93 | 88 | 70 |
| D-04 | 86 | 91 | 87 | 70 |
| D-05 | 90 | 98 | 92 | 85 |
| D-06 | 87 | 85 | 72 | 61 |
| D-07 | 93 | 92 | 88 | 71 |
| D-08 | 91 | 96 | 94 | 81 |

Statistical calculation was performed for hCG activity [IU/ml] to evaluate the influence and interaction of arginine and methionine. The result of the statistical evaluation confirms that arginine has a statistical significant influence on hCG immunoassay stability results. Methionine content has a minor influence at 25° C. on hCG immunoassay stability results. It becomes clear that over a low (0.1 mg/ml) concentration of methionine no further increase in stability by increasing the concentration even up to 1.5 mg/ml is detectable. There is no statistical significant interaction between arginine and methionine for this response parameter.

6.5.3 Oxidized Proteins

In the above stability studies it was surprisingly observed that the presence of arginine has a tremendously stabilizing effect. However, addition of arginine resulted in an increased level of oxidized proteins. Methionine can be added to prevent this oxidation and this study investigates the concentration balance between arginine as stabilizer and methionine as antioxidant.

Stability results of amount of oxidized proteins [% increase from initial] during storage for 6 months at 25±2° C./60±5% RH and 3 month at 30±2° C./65±5% RH for formulations with arginine and Methionine (in the concentration range 0.1-1.5 mg/ml) are listed below. For comparison formulation E-09 with arginine and without methionine is also included in Table 14 Table.

TABLE 14

Results of oxidized proteins during storage at 25 ± 2° C./60 ± 5% RH and 30 ± 2° C./65 ± 5% RH. The full description of all formulations is given in Table 11.

| | Oxidized proteins [% increase from initial] | | | | | | |
|---|---|---|---|---|---|---|---|
| | 30° C. ± 2° C./65 ± 5% RH | | | 25° C. ± 2° C./60 ± 5% RH | | | |
| Formulation | 1 month | 2 months | 3 months | 1 month | 2 months | 3 months | 6 months |
| D-01 | 5.5 | 4.1 | 8.3 | 10.1 | 4.1 | 9.6 | 6.9 |
| D-02 | 9.9 | 8.5 | 10.3 | 11.7 | 11.7 | 6.6 | 8.5 |
| D-03 | 10.9 | 10.0 | 11.4 | 12.3 | 13.3 | 11.8 | 12.8 |
| D-04 | 8.9 | 8.4 | 8.9 | 8.9 | 11.2 | 9.8 | 8.9 |
| D-05 | 12.9 | 13.8 | 13.8 | 13.3 | 20.5 | 11.0 | 15.2 |
| D-06 | 7.0 | 9.8 | 11.6 | 10.7 | 7.9 | 9.3 | 11.2 |
| D-07 | 14.0 | 10.1 | 11.1 | 14.5 | 13.5 | 15.0 | 10.1 |
| D-08 | 7.6 | 9.5 | 7.6 | 13.3 | 9.0 | 11.8 | 7.6 |
| E-09 (no L-methionine) | — | — | 241 | — | — | — | — |

From Table 14 Table it is surprisingly seen that even small quantities of methionine are enough to prevent oxidation in the entire concentration range of arginine.

6.5.4 Summary of DoE

To conclude and summarize the results of the DoE, the response optimizer in Minitab was applied, see FIG. 2. The Minitab Response Optimizer tool shows how different experimental factor settings e.g. arginine and methionine concentrations affect the predicted responses e.g. the FSH immunoassay [IU/ml] and the hCG immunoassay [IU/ml] for the factorial design. The optimization plot shows the effect of each factor (columns) on the responses (rows). The vertical bold lines on the graph represent the current factor settings. The numbers displayed at the top of a column show the current factor level settings (in squared brackets). The horizontal dashed lines and corresponding numbers represent the responses for the current factor level. The response optimizer will be based on 25° C. results. The result of applying the response optimizer is depicted FIG. 2. The best stability (composite desirability) is obtained at high concentrations of arginine and low concentrations of methionine.

6.6 pH Study

In the buffer capacity study it was shown that a buffering agent was not necessary in the hMG formulation, by using only arginine to stabilize the pH in the desired pH range.

To confirm that the pH is maintained during storage, it was measured during 6 months of storage at 25±2° C./60±5% RH and 3 months at 30±2° C./65±5% RH. The results are listed in Table 15.

Target pH for all formulations was pH 6.8 and pH of all formulations was 6.8 at the initial time point. pH was fairly stable but increased slightly to about 6.9 after 2 months and maintained a pH around 6.9 up to 6 months of storage. Results up to 6 months of storage confirm stability of pH in the tested concentration range of arginine.

TABLE 15

| | Results of pH study | | | | | |
|---|---|---|---|---|---|---|
| | | | 30° C. ± 2° C./65 ± 5% RH | | 25° C. ± 2° C./60 ± 5% RH | |
| pH | | | 2 | 3 | 2 | 3 | 6 |
| Formulation | Initial | month | months | months | months | months |
| D-01 | 6.8 | 6.9 | 6.9 | 6.9 | 6.9 | 6.9 |
| D-02 | 6.8 | 6.9 | 6.9 | 6.9 | 6.9 | 6.8 |

TABLE 15-continued

| | Results of pH study | | | | | |
|---|---|---|---|---|---|---|
| | | | 30° C. ± 2° C./65 ± 5% RH | | 25° C. ± 2° C./60 ± 5% RH | |
| pH | | | 2 | 3 | 2 | 3 | 6 |
| Formulation | Initial | month | months | months | months | months |
| D-03 | 6.8 | 6.9 | 6.9 | 6.9 | 6.9 | 6.8 |
| D-04 | 6.8 | 6.9 | 6.9 | 6.9 | 6.9 | 6.8 |
| D-05 | 6.8 | 6.9 | 6.9 | 6.9 | 6.9 | 6.8 |
| D-06 | 6.8 | 6.9 | 6.9 | 6.9 | 6.9 | 6.8 |
| D-07 | 6.8 | 6.9 | 6.9 | 6.9 | 6.9 | 6.8 |
| D-08 | 6.8 | 6.9 | 6.9 | 6.9 | 6.9 | 6.9 |

7 Conclusion

Very surprisingly, the buffer capacity of the hMG formulation with no buffer is higher than the reference with 1 mM Di-sodium hydrogen phosphate dodecahydrate. The main excipient component in the hMG formulation is arginine. The pKa values for arginine are $pKa_1=2.17$; $pKa_2=9.04$ and $pKa_3=12.5$. It is unexpected that arginine exhibits sufficient buffering behaviour far from its pKa values. The results however clearly show that no—additional buffering agent is needed in the hMG formulation in the current pH range. Arginine alone is sufficient to maintain the pH in the desired pH range. Stability of the pH was confirmed in the DoE study testing a concentration range of arginine during 6 months storage at 25±2° C./60±5% RH and 3 months storage at 30±2° C./65±5% RH which confirmed the observations in the buffer capacity study.

Addition of arginine to the inventive liquid hMG formulation was shown to have a tremendously stabilizing effect on liquid hMG formulations. However, arginine was also found to result in a high level of oxidized proteins. Addition of methionine was shown to prevent oxidation compared to a formulation without methionine.

During 6 months of storage at 25±2° C./60±5% RH and 3 months of storage at 30±2° C./65±5% RH, it was shown that even a small concentration of methionine prevents oxidation.

Concluding the results from these studies it is clearly seen that the addition of arginine is sufficient to maintain pH at the desired pH level. Addition of arginine stabilizes the tested gonadotropin formulation tremendously in a liquid formulation. No other of the tested amino acid, sugar or salt showed a similar stabilizing effect. The level of oxidized proteins is increased significantly by addition of arginine, however addition of even low amounts of methionine prevents protein oxidation. Surprisingly, even small quantities of methionine are sufficient to prevent oxidation independently of the concentration of arginine.

Example 2

The present inventors further confirmed that the present advantageous inventive formulation would also be suitable to stabilize the respective recombinant gonadotropin formulation.

To that avail, recombinant FSH and recombinant hCG (with the sequences as described above, respectively) were prepared according to well known methods.

An accelerated stability study was carried out for two formulations, comprising rhCG or rFSH, respectively, as described below.

The observed surprising stabilising effect of arginine has also been confirmed in recombinant proteins. Both rFSH and rhCG have been formulated in 5 mg/ml phenol, 0.15 mg/ml L-methionine, 150 mM arginine HCl, 0.005 mg/ml polysorbate 20, pH 6.8. To simplify the analysis of the protein stability, rFSH and rhCG were formulated in different containers.

TABLE 16

| | Immunoactivity (IU/ml) | | | | |
|---|---|---|---|---|---|
| | Initial | 1 month, 30° C. | 2 months, 30° C. | 4 months, 30° C. | 16 months, 5° C. |
| FSH [33.3 µg/ml] | 464 | 444 | 456 | 469 | 435 |
| rhCG [50 µg/ml] | 711 | 680 | 656 | 600 | 685 |

| | SEC (Purity of rFSH, %) | | | | |
|---|---|---|---|---|---|
| | Initial | 1 month, 30° C. | 2 months, 30° C. | 4 months, 30° C. | 16 months, 5° C. |
| FSH [33.3 µg/ml] | 98.9 | 98.6 | 98.3 | 97.9 | 96.9 |

| | HIC (Purity of rhCG, %) | | | | |
|---|---|---|---|---|---|
| | Initial | 1 month, 30° C. | 2 months, 30° C. | 4 months, 30° C. | 14 months, 5° C. |
| rhCG [50 µg/ml] | 98.8 | 96.8 | 93.3 | 89.4 | 99.9 |

This fully confirms that the present inventive formulation with arginine, but no additional buffer, and with a low amount of methionine is suitable to stabilized recombinant gonadotropins as well.

Example 3

Further studies were conducted, wherein the following composition was assessed:

TABLE 17

Composition for liquid hMG 625 IU/ml formulation

| Batch no. | Buffer[1] | Surfactant | Preservative | Antioxidant | Stabilizer/ Tonicity agent |
|---|---|---|---|---|---|
| J-01 | No buffer pH 6.8 | 0.005 mg/ml Polysorbate 20 | 5.0 mg/ml Phenol | 0.15 mg/ml L-Methionine | 150 mM L-arginine HCl |

[1]pH is adjusted with 0.2N HCl/NaOH

Stability of Target Formulation

Combining all previous results, the good stability was confirmed for the above formulation, as follows:

TABLE 18

FSH immunoassay
Stability results of FSH immunoassay during storage for 3 months at 25 ± 2° C./60 ± 5% relative humidity (RH) and 12 months at 5 ± 3° C.:
Results of FSH immunoassay during storage at 25 ± 2° C./60 ± 5% RH, and 12 months at 5 ± 3° C.

| | 25° C. ± 2° C./ 60 ± 5% RH | | | 5° C. ± 3° C. | |
|---|---|---|---|---|---|
| FSH [% of initial] | 1 | 2 | 3 | 3 | 12 |
| Formulation | Initial | month | months | months | months | months |
| J-01 | 100 | 95.2 | 95.9 | 98.8 | 96.8 | 100.5 |

The results confirm the stability as determined by FSH immunoassay.

TABLE 19 hCG immunoassay
Stability results of hCG immunoassay during storage for 1 month at 25 ± 2° C./60 ± 5% RH is listed in Table 19 and 12 months at 5 ± 3° C.
Results of hCG immunoassay during storage at 25 ± 2° C./60 ± 5% RH and 12 months at 5 ± 3° C.

| | 25° C. ± 2° C./ | |
| hCG [% of initial] | 60 ± 5% RH | 5° C. ± 3° C. |
|---|---|---|---|
| Formulation | Initial | 1 month | 3 months | 12 months |
| J-01 | 100 | 88.3 | 94.1 | 89.5 |

The results confirm the stability as determined by hCG immunoassay.

TABLE 20

Oxidized proteins
Stability results of amount of oxidized proteins [% increase from initial] during storage for 3 months at 25 ± 2° C./ 60 ± 5% RH and 12 months at 5 ± 3° C.
Results of oxidized proteins during storage at 25 ± 2° C./ 60 ± 5% RH and 12 months at 5 ± 3° C.

| Oxidized proteins [% increase from initial] | 25° C. ± 2° C./60 ± 5% RH | | | 5° C. ± 3° C. | |
|---|---|---|---|---|---|
| Formulation | 1 month | 2 months | 3 months | 3 months | 12 months |
| J-01 | 1.8 | 5.7 | 7.9 | 2.6 | 11 | pH

Stability results of pH during storage for 3 months at 25±2° C./60±5% RH and 12 months at 5±3° C. show a stable pH.

TABLE 21

Results of pH during storage at 25 ± 2° C./60 ± 5% RH and 12 months at 5 ± 3° C.

| pH | | 25° C. ± 2° C./ 60 ± 5% RH | | | 5° C. ± 3° C. | |
|---|---|---|---|---|---|---|
| Formulation | Initial | 1 months | 2 months | 3 months | 3 months | 12 months |
| J-01 | 6.9 | 6.7 | 6.8 | 6.7 | 6.7 | 6.8 |

Example 4

In addition to the above, the present inventors also performed a bioassay study (6 months storage at 25° C. for the DoE batches).

FSH Bioassay (Steelman-Pohley)

Stability results of the FSH bioassay during storage for 6 months at 25±2° C./60±5% RH are listed in Table 22.

TABLE 22

Results of FSH bioassay during storage at 25 ± 2° C./60 ± 5% RH. The full description of all formulations is given in Table 11.

| FSH [% of stated potency (600 IU/ml)] Formulation | 25° C. ± 2° C./ 60 ± 5% RH 6 months |
|---|---|
| D-01 | 98.8 |
| D-02 | 100.7 |
| D-03 | 102.0 |
| D-04 | 104.7 |
| D-05 | 103.4 |
| D-06 | 101.0 |
| D-07 | 102.6 |
| D-08 | 104.9 |

The results confirm the stability, as determined by FSH bioassay.

LH Bioassay (Seminal Weight Gain)

Stability results of LH bioassay during storage for 6 months at 25±2° C./60±5% RH is listed in Table 23.

TABLE 23

Results of LH bioassay during storage at 25 ± 2° C./60 ± 5% RH. The full description of all formulations is given in Table 11.

| LH [% of stated potency (600 IU/ml)] Formulation | 25° C. ± 2° C./ 60 ± 5% RH 6 months |
|---|---|
| D-01 | 87.8 |
| D-02 | 101.3 |
| D-03 | 90.9 |
| D-04 | 95.6 |
| D-05 | 97.5 |
| D-06 | 95.0 |
| D-07 | 97.3 |
| D-08 | 100.1 |

The results confirm the stability, as determined by LH bioassay.

Furthermore, the composition of Example 3 was also tested in an FSH and LH bioassay, with the following results:

Stability results of FSH bioassay during storage for 3 months at 25±2° C./60±5% RH and 12 months at 5±3° C. are listed in Table 24:

TABLE 24

Results of FSH bioassay during storage at 25 ± 2° C./ 60 ± 5% RH and 12 months at 5 ± 3° C.

| FSH [% of stated potency (625 IU/ml)] | | 25° C. ± 2° C./ 60 ± 5% RH | | | 5° C. ± 3° C. | |
|---|---|---|---|---|---|---|
| Formulation | Initial | 1 month | 2 months | 3 months | 3 months | 12 months |
| J-01 | 94.7 | 93.6 | 94.5 | 97.6 | 95.8 | 96.1 |

The results confirm the stability determined by FSH bioassay.

Stability results of LH bioassay during storage for 3 months at 25±2° C./60±5% RH and 12 months at 5±3° C. is listed in Table 25.

TABLE 25

Results of LH bioassay during storage at 25 ± 2° C./ 60 ± 5% RH and 12 months at 5 ± 3° C.

| LH [% of stated potency (625 IU/ml)] | | 25° C. ± 2° C./ 60 ± 5% RH | | | 5° C. ± 3° C. | |
|---|---|---|---|---|---|---|
| Formulation | Initial | 1 month | 2 months | 3 months | 3 months | 12 months |
| J-01 | 102.1 | 102.2 | 99.0 | 100.0 | 101.5 | 100.0 |

The results confirm the stability determined by LH bioassay.

8 Abbreviations and Definitions

BP British Pharmacopeia
DoE Design of experiment
DS Drug substance

FSH Follicle-stimulating hormone
hCG Human chorionic gonadotropin
hMG Human menopausal gonadotropin
hMG-HP Human menopausal gonadotropin-Highly purified
JP Japanese Pharmacopeia
LH Luteinizing hormone
MD Multiple dose
NF National Formulary
Ph Eur European Pharmacopeia
PS 20 Polysorbate 20
USP U.S. Pharmacopeia
WFI Water for injection

The invention claimed is:

1. A liquid pharmaceutical formulation comprising a gonadotropin, 50-160 mM arginine, and 0.05-1.5 mg/mL methionine, wherein the formulation does not additionally comprise a buffer, and wherein the pH of the formulation is between 6.0 and 7.5.

2. The pharmaceutical formulation of claim 1, wherein the gonadotropin comprises hCG (human chorionic gonadotropin), and optionally FSH and/or LH.

3. The pharmaceutical formulation of claim 1, wherein the gonadotropin comprises hMG (human menopausal gonadotropin).

4. The pharmaceutical formulation of claim 3, wherein the hMG is present in an amount of 300-900 IU/mL.

5. The pharmaceutical formulation of claim 3, wherein the hMG is present in an amount of 500-700 IU/mL.

6. The pharmaceutical formulation of claim 3, wherein the hMG is present in an amount of 600-650 IU/mL.

7. The pharmaceutical formulation of claim 3, wherein the hMG is present in an amount of about 625 IU/mL.

8. The pharmaceutical formulation of claim 1, wherein the gonadotropin comprises human origin, urinary-derived FSH, LH and/or hCG.

9. The pharmaceutical formulation of claim 1, wherein the gonadotropin comprises recombinant FSH, LH and/or hCG.

10. The pharmaceutical formulation of claim 1, further comprising a preservative.

11. The pharmaceutical formulation of claim 10, wherein the preservative is phenol.

12. The pharmaceutical formulation of claim 11, wherein the phenol is present in an amount of 4.0-6.0 mg/mL.

13. The pharmaceutical formulation of claim 1, further comprising a surface active agent.

14. The pharmaceutical formulation of claim 13, wherein the surface active agent is polysorbate 20.

15. The pharmaceutical formulation of claim 14, wherein the polysorbate 20 is present in an amount of 0.001-0.05 mg/mL.

16. The pharmaceutical formulation of claim 1, wherein the arginine is present in an amount of 80-160 mM.

17. The pharmaceutical formulation of claim 1, wherein the arginine is present in an amount of about 150 mM.

18. The pharmaceutical formulation of claim 1, wherein the arginine is L-arginine HCl.

19. The pharmaceutical formulation of claim 1, wherein the methionine is present in an amount of about 0.15 mg/mL methionine.

20. The pharmaceutical formulation of claim 1, wherein the pH of the formulation is 6.5-7.4.

21. The pharmaceutical formulation of claim 1, wherein the pH of the formulation is 6.5-7.1.

22. A method for treating infertility in a subject in need thereof, the method comprising administering the liquid pharmaceutical formulation of claim 1 to the subject.

* * * * *

```
                        SEQUENCE LISTING

<160> NUMBER OF SEQ ID NOS: 4

<210> SEQ ID NO 1
<211> LENGTH: 116
<212> TYPE: PRT
<213> ORGANISM: Homo sapiens
<220> FEATURE:
<221> NAME/KEY: SIGNAL
<222> LOCATION: 1..24
<223> OTHER INFORMATION: leader peptide

<400> SEQUENCE: 1

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

<210> SEQ ID NO 2
<211> LENGTH: 129
<212> TYPE: PRT
<213> ORGANISM: Homo sapiens
<220> FEATURE:
<221> NAME/KEY: SIGNAL
<222> LOCATION: 1..18
<223> OTHER INFORMATION: leader peptide

<400> SEQUENCE: 2

Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110
```

```
Thr Val Arg Gly Leu Gly Pro Ser Tyr Cys Ser Phe Gly Glu Met Lys
        115                 120                 125

Glu

<210> SEQ ID NO 3
<211> LENGTH: 165
<212> TYPE: PRT
<213> ORGANISM: Homo sapiens
<220> FEATURE:
<221> NAME/KEY: SIGNAL
<222> LOCATION: 1..20
<223> OTHER INFORMATION: leader peptide

<400> SEQUENCE: 3

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 4
<211> LENGTH: 141
<212> TYPE: PRT
<213> ORGANISM: Homo sapiens
<220> FEATURE:
<221> NAME/KEY: SIGNAL
<222> LOCATION: 1..20
<223> OTHER INFORMATION: leader peptide

<400> SEQUENCE: 4

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95
```

```
Asp Pro Val Val Ser Phe Pro Val Ala Leu Ser Cys Arg Cys Gly Pro
            100             105                 110

Cys Arg Arg Ser Thr Ser Asp Cys Gly Gly Pro Lys Asp His Pro Leu
        115             120                 125

Thr Cys Asp His Pro Gln Leu Ser Gly Leu Leu Phe Leu
    130             135                 140
```